US012734364B2

(12) United States Patent
Gross et al.

(10) Patent No.: US 12,734,364 B2
(45) Date of Patent: Sep. 15, 2026

(54) AORTIC CARDIAC PACING AND SENSING

(71) Applicant: SMARTVALVES LTD., Savyon (IL)

(72) Inventors: Yossi Gross, Moshav Mazor (IL); Meni Iamberger, Kfar Saba (IL); Navot Rabban, Ramat Gan (IL)

(73) Assignee: SMARTVALVES LTD., Savyon (IL)

( * ) Notice: Subject to any disclaimer, the term of this patent is extended or adjusted under 35 U.S.C. 154(b) by 0 days.

(21) Appl. No.: 19/381,343

(22) Filed: Nov. 6, 2025

(65) Prior Publication Data

US 2026/0158279 A1 Jun. 11, 2026

Related U.S. Application Data

(60) Provisional application No. 63/849,212, filed on Jul. 23, 2025, provisional application No. 63/849,229, filed on Jul. 23, 2025, provisional application No. 63/809,535, filed on May 21, 2025, provisional application No. 63/717,923, filed on Nov. 8, 2024.

(51) Int. Cl.

| | |
|---|---|
| ***A61N 1/362*** | (2006.01) |
| ***A61F 2/24*** | (2006.01) |
| ***A61N 1/05*** | (2006.01) |

(52) U.S. Cl.
CPC ............ *A61N 1/362* (2013.01); *A61F 2/2418* (2013.01); *A61N 1/056* (2013.01)

(58) Field of Classification Search
CPC ....... A61F 2/2418; A61N 1/056; A61N 1/057; A61N 1/3629; A61N 1/362
See application file for complete search history.

(56) References Cited

U.S. PATENT DOCUMENTS

| | | | | |
|---|---|---|---|---|
| 5,487,760 | A | 1/1996 | Villafana | |
| 7,643,879 | B2 | 1/2010 | Shuros et al. | |
| 8,204,605 | B2 | 6/2012 | Hastings et al. | |
| 9,326,854 | B2 | 5/2016 | Casley et al. | |
| 9,808,201 | B2 | 11/2017 | Braido et al. | |
| 10,543,083 | B2 | 1/2020 | Gross | |
| 10,835,750 | B2 | 11/2020 | Gross | |
| 11,013,597 | B2 | 5/2021 | Gross | |
| 11,065,451 | B1 * | 7/2021 | Gross ................. | A61N 1/37229 |

(Continued)

FOREIGN PATENT DOCUMENTS

| | | | |
|---|---|---|---|
| EP | 3 785 758 | A1 | 3/2021 |
| EP | 3 508 113 | B1 | 8/2024 |

(Continued)

*Primary Examiner* — George R Evanisko
(74) *Attorney, Agent, or Firm* — Sughrue Mion, PLLC

(57) ABSTRACT

A method is provided for delivering ventricular pacing pulses, the method including positioning a first electrode in contact with left ventricular endocardium of a left ventricular outflow tract (LVOT) at a first-electrode site having a first-electrode angular location, with respect to an axis of the LVOT; and positioning a second electrode in contact with the left ventricular endocardium of the LVOT at a second-electrode site having a second-electrode angular location with respect to the axis of the LVOT, the second-electrode angular location different from the first-electrode angular location. Circuitry is activated to deliver the ventricular pacing pulses by driving a pacing signal between the first and the second electrodes. Other embodiments are also described.

29 Claims, 13 Drawing Sheets

(56) References Cited

U.S. PATENT DOCUMENTS

| | | | |
|---|---|---|---|
| 11,185,703 | B2 | 11/2021 | Shuros et al. |
| 11,291,844 | B2 | 4/2022 | Gross |
| 11,331,476 | B2 | 5/2022 | Capek et al. |
| 11,931,255 | B1 | 3/2024 | Gross et al. |
| 11,975,203 | B1 | 5/2024 | Gross et al. |
| 2011/0196482 | A1 | 8/2011 | Forsell |
| 2012/0296382 | A1 | 11/2012 | Shuros et al. |
| 2016/0045316 | A1 | 2/2016 | Braido et al. |
| 2017/0027689 | A1 | 2/2017 | Marcelli |
| 2017/0258585 | A1 | 9/2017 | Marquez et al. |
| 2017/0304624 | A1 | 10/2017 | Friedman et al. |
| 2019/0247651 | A1 | 8/2019 | Reider |
| 2022/0287851 | A1 | 9/2022 | Goldberg et al. |
| 2023/0218180 | A1 | 7/2023 | Mujeeb-U-Rahman et al. |
| 2023/0329865 | A1 | 10/2023 | Kappetein |
| 2024/0164642 | A1 | 5/2024 | Hunter et al. |
| 2025/0058124 | A1 | 2/2025 | Gross et al. |

FOREIGN PATENT DOCUMENTS

| | | | |
|---|---|---|---|
| WO | 2015/200707 | A1 | 12/2015 |
| WO | 2018/142186 | A1 | 8/2018 |
| WO | 2020/257759 | A1 | 12/2020 |
| WO | 2021/224904 | A1 | 11/2021 |
| WO | 2022/051716 | A1 | 3/2022 |
| WO | 2022/149130 | A1 | 7/2022 |
| WO | 2025/041129 | A1 | 2/2025 |

* cited by examiner

EXTERNAL CONTROL UNIT
50
14
10
20
52
20
24,26
29
28
36
40
30
110,130
16
32
34,34A,56
34,34B,56
34,34A,54
102
22,27
34,34A
106
92
90
70,92
86
96
76B
34,54
80
76A
72
70,74,92
70,92
22,27

AORTIC CARDIAC PACING AND SENSING

CROSS-REFERENCE TO RELATED APPLICATIONS

The present application claims priority from:

U.S. Provisional Application 63/717,923, filed Nov. 8, 2024,

U.S. Provisional Application 63/809,535, filed May 21, 2025,

U.S. Provisional Application 63/849,212, filed Jul. 23, 2025, and

U.S. Provisional Application 63/849,229, filed Jul. 23, 2025.

All the above-mentioned applications are assigned to the assignee of the present application and incorporated herein by reference.

FIELD OF THE APPLICATION

The present invention relates generally to surgical implants and systems, and specifically to aortic cardiac pacing implants, systems, and methods.

BACKGROUND OF THE APPLICATION

Aortic heart valve replacement may be necessary to treat valve regurgitation or stenotic calcification of the leaflets. In percutaneous transluminal delivery techniques, a prosthetic aortic valve is compressed for delivery in a catheter and advanced through the descending aorta to the heart, where the prosthetic valve is deployed in the aortic valve annulus. New-onset transient and permanent cardiac conduction disturbances are common after transcatheter aortic valve replacement (TAVR). The most common complication is left bundle branch block (LBBB). As a guideline, all TAVR patients receive, upon completion of the procedure, a temporary (non-implanted) pacemaker for the first 24-72 hours after the procedure. This has a high rate of adverse events, including lead dislodgement, cardiac perforation, pulmonary embolism, and infections.

PCT Publication WO 2022/149130 to Gross, which is incorporated herein by reference, inter alia describes a prosthetic aortic valve, which is configured to be delivered to a native aortic valve of a patient in a constrained delivery configuration within a delivery sheath. The prosthetic aortic valve includes a frame, which includes interconnected stent struts arranged so as to define interconnected stent cells; a plurality of prosthetic leaflets coupled to the frame; a cathode and an anode, which are mechanically coupled to the frame; and a prosthetic-valve coil, which is in non-wireless electrical communication with the cathode and the anode, and is coupled to a plurality of the stent struts, running along the stent struts so as to surround a plurality of the stent cells when the prosthetic aortic valve is in an expanded fully-deployed configuration upon release from the delivery sheath.

PCT Publication WO 2025/041129 to Gross et al., which is incorporated herein by reference, describes a prosthetic cardiac valve that includes a frame and a plurality of prosthetic leaflets coupled to the frame so as to allow blood flow in one direction. An antenna is mechanically coupled to the frame proximal of the prosthetic leaflets, and includes one or more prosthetic-valve coils. First and second proximal peaks respectively defined by circumferentially adjacent first and second proximal-most stent cells of interconnected stent cells of the frame are located at respective first and second peak angular locations about a central longitudinal axis of the frame. The antenna is mechanically coupled to the frame such that a centroid of the antenna is at an antenna angular location between the first and the second peak angular locations, and a proximal-most point of the antenna is axially disposed between 5 mm proximal of and 5 mm distal of the first and the second proximal peaks. Other embodiments are also described.

US Patent Application Publication 2017/0258585 to Marquez et al. describes sensor-integrated prosthetic valves that can comprise a variety of features, including a plurality of valve leaflets, a frame assembly configured to support the plurality of valve leaflets and define a plurality of commissure supports terminating at an outflow end of the prosthetic valve, a sensor device associated with the frame assembly and configured to generate a sensor signal, for example, a sensor signal indicating deflection of one or more of the plurality of commissure supports, and a transmitter assembly configured to receive the sensor signal from the sensor device and wirelessly transmit a transmission signal that is based at least in part on the sensor signal.

U.S. Pat. No. 9,326,854 to Casley et al. describes medical device delivery assemblies. The assembly may include a catheter-based delivery system. The assembly may include a pacing element to pace a patient's heart before, during, or after a procedure. The pacing element may be a detachable, implanting pacing element. The pacing element may be an implantable pacemaker and the implantable pacemaker may be disposed on a catheter-based delivery system. The assembly may include a prosthetic heart valve with one or more pacing elements on it. The pacing element may include a pacing strip or strips. These strips may be conductive or insulative. These strips May prevent, treat, or correct abnormal electrical communication in a heart.

SUMMARY OF THE APPLICATION

In some embodiments of the present invention, a method is provided for delivering ventricular pacing pulses to a heart of a patient, the method generally comprising placing first and second electrodes in contact with left ventricular endocardium of a left ventricular outflow tract (LVOT) at a first-electrode site and a second-electrode site, respectively. The ventricular pacing pulses are delivered by driving a pacing signal between the first and the second electrodes, optionally by activating circuitry of a prosthetic cardiac valve system.

In some embodiments of the present invention, a method is provided for delivering ventricular pacing pulses to the heart, the method generally comprising placing a first electrode in contact with left ventricular endocardium of the LVOT at a first-electrode site, and a second electrode at a second-electrode site in electrical communication with the patient's body, such as in the aorta (optionally angularly aligned with first-electrode angular location), elsewhere within the patient's body (such as in contact with the heart, e.g., pericardium of the heart), or on an external surface of skin of the patient's body, e.g., using a patch electrode). The ventricular pacing pulses are delivered by driving a pacing signal between the first and the second electrodes, optionally by activating circuitry of a prosthetic cardiac valve system.

In some embodiments of the present invention, a method is provided for sensing electrical activity of the heart, the method generally comprising placing first and second electrodes in contact with left ventricular endocardium of the LVOT at a first-electrode site and a second-electrode site, respectively. The electrical activity of the heart is sensed between the first and the second electrodes. Typically, circuitry is activated to attempt to identify a ventricular activation signal in an intracardiac electrogram (EGM) sensed using the first and the second electrodes.

In some applications of the present invention, the above-mentioned prosthetic cardiac valve system comprises a prosthetic aortic valve, which is configured to be implanted at an aortic position in the heart, and which comprises a plurality of prosthetic leaflets, a frame, and one or more electrodes, including a cathode and an anode, mechanically coupled to the frame. The prosthetic aortic valve further comprises a prosthetic-valve coil, which is in non-wireless electrical communication with the cathode and the anode.

For some applications, the prosthetic aortic valve further comprises circuitry, which is configured to apply pacing to the heart using the one or more electrodes. For example, the pacing may be applied temporarily for up to several months after implantation of the prosthetic aortic valve, typically using an external control unit to continuously provide power, or applied longer-term, in which case the prosthetic aortic valve may further comprise an energy storage module, e.g., comprising a battery, which may be periodically charged using the external control unit. Further alternatively or additionally, for some applications, the circuitry is configured to apply rapid pacing during an invasive structural heart procedure, such as an implantation procedure, such as a transcatheter aortic valve replacement (TAVR).

There is therefore provided, in accordance with an application of the present invention, a prosthetic cardiac valve system including a prosthetic cardiac valve, which is configured to be delivered to a native cardiac valve of a heart of a patient in a constrained delivery configuration, the prosthetic cardiac valve including:

a frame, which includes interconnected stent cells, which include distal upstream stent cells that are located in a distal upstream half of the frame and are shaped so as to define respective distal upstream peaks;

a plurality of prosthetic leaflets coupled to the frame so as to allow blood flow in a proximal downstream direction and inhibit blood flow in a distal upstream direction when the prosthetic cardiac valve is in an expanded deployment configuration;

electrodes, which include a plurality of distal upstream electrodes mechanically coupled to the frame at or near respective ones of the distal upstream peaks; and circuitry, which is electrically coupled to the electrodes, and which is configured to apply ventricular pacing to the heart by activating one or more of the distal upstream electrodes as one or more anodes and one or more of the other distal upstream electrodes as one or more cathodes.

For some applications, the distal upstream electrodes are mechanically coupled to the frame at or within 8 mm of the respective ones of the distal upstream peaks.

For some applications, the distal upstream stent cells are distal-most ones of the stent cells.

For some applications, the prosthetic cardiac valve is a prosthetic aortic valve.

For some applications, the prosthetic cardiac valve is a prosthetic atrioventricular valve.

There is further provided, in accordance with an application of the present invention, a method including:

delivering a prosthetic cardiac valve of a prosthetic cardiac valve system to a native cardiac valve of a heart of a patient in a constrained delivery configuration, the prosthetic cardiac valve including (a) a frame, which includes interconnected stent cells, which include distal upstream stent cells that are located in a distal upstream half of the frame and are shaped so as to define respective distal upstream peaks; (b) a plurality of prosthetic leaflets coupled to the frame; and (c) electrodes, which include a plurality of distal upstream electrodes mechanically coupled to the frame at or near respective ones of the distal upstream peaks;

transitioning the prosthetic cardiac valve to an expanded deployment configuration in which the plurality of prosthetic leaflets allow blood flow in a downstream direction and inhibit blood flow in an upstream direction; and activating circuitry, which is electrically coupled to the electrodes, to apply ventricular pacing to the heart by activating one or more of the distal upstream electrodes as one or more anodes and one or more of the other distal upstream electrodes as one or more cathodes.

There is still further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location with respect to an axis of the LVOT, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode at a second-electrode site that is (a) in electrical communication with a body of the patient, and (b) outside all chambers of the heart; and activating circuitry to deliver the ventricular pacing pulses by driving a pacing signal between the first and the second electrodes.

There is additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode at a second-electrode site that is (a) in electrical communication with a body of the patient, and (b) outside all chambers of the heart; and activating circuitry to deliver the ventricular pacing pulses by driving a pacing signal between the first and the second electrodes.

There is yet additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to an aorto-mitral curtain, below a non-coronary cusp (NCC)-left coronary cusp (LCC) interleaflet triangle, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and the LCC;

positioning a second electrode at a second-electrode site that is (a) in electrical communication with a body of the patient, and (b) outside all chambers of the heart; and activating circuitry to deliver the ventricular pacing pulses by driving a pacing signal between the first and the second electrodes.

There is further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a left fibrous trigone, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode at a second-electrode site that is (a) in electrical communication with a body of the patient, and (b) outside all chambers of the heart; and activating circuitry to deliver the ventricular pacing pulses by driving a pacing signal between the first and the second electrodes.

There is still further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a right side of the muscular part of a ventricular septum, below a right coronary cusp (RCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode at a second-electrode site that is (a) in electrical communication with a body of the patient, and (b) outside all chambers of the heart; and activating circuitry to deliver the ventricular pacing pulses by driving a pacing signal between the first and the second electrodes.

There is additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to the muscular part of a ventricular septum, below an anterior side of a left coronary cusp (LCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and the LCC;

positioning a second electrode at a second-electrode site that is (a) in electrical communication with a body of the patient, and (b) outside all chambers of the heart; and activating circuitry to deliver the ventricular pacing pulses by driving a pacing signal between the first and the second electrodes.

There is yet additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a right fibrous trigone, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode at a second-electrode site that is (a) in electrical communication with a body of the patient, and (b) outside all chambers of the heart; and activating circuitry to deliver the ventricular pacing pulses by driving a pacing signal between the first and the second electrodes.

For some applications, the second-electrode site is on an external surface of skin of the patient's body.

For some applications, the second-electrode site is in contact with pericardium of the heart.

For some applications, the second-electrode site is within myocardium of the heart.

There is also provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location with respect to an axis of the LVOT, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, the second-electrode angular location different from the first-electrode angular location, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, the second-electrode angular location different from the first-electrode angular location, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

For some applications, the first-electrode angular location is adjacent to a membranous septum, below a right lateral end of the NCC.

For some applications, the first-electrode angular location is adjacent to a membranous septum, below a right lateral end of the RCC.

For some applications, the second-electrode angular location is adjacent to a right fibrous trigone, below the middle of the NCC.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location is adjacent to the left lateral end of the muscular part of a ventricular septum closest to a left fibrous trigone.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location is adjacent to an aorto-mitral curtain, below an NCC-LCC interleaflet triangle.

For some applications:

the first-electrode angular location is adjacent to a membranous septum, below a right lateral end of the RCC, and the second-electrode angular location is adjacent to an aorto-mitral curtain, below a left-lateral end of the NCC.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location adjacent to a left fibrous trigone.

For some applications:

the first-electrode angular location is adjacent to a membranous septum, below a right lateral end of the NCC, and the second-electrode angular location is adjacent to an anterior end of the left fibrous trigone and a left lateral end of the muscular part of a ventricular septum.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications:

the first-electrode angular location is adjacent to a membranous septum, below a right lateral end of the NCC, and the second-electrode angular location is adjacent to an aorto-mitral curtain and a posterior end of the left fibrous trigone.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications:

- the first-electrode angular location is adjacent to a membranous septum, below a right lateral end of the RCC, and
- the second-electrode angular location is adjacent to an anterior end of the left fibrous trigone and a left lateral end of the muscular part of a ventricular septum.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications:

- the first-electrode angular location is adjacent to a membranous septum, below a right lateral end of the RCC, and
- the second-electrode angular location is an aorto-mitral curtain and a posterior end of the left fibrous trigone.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location is along adjacent to a right fibrous trigone, below the middle of the NCC.

For some applications, the second-electrode angular location is along adjacent to the left lateral end of the muscular part of a ventricular septum closest to a left fibrous trigone.

There is still further provided, in accordance with an application of the present invention, a method for delivering ventricular pacing pulses to a heart of a patient, the method including:

- positioning a first electrode in contact with left ventricular endocardium of a left ventricular outflow tract (LVOT) at a first-electrode site having:
  - a first-electrode angular location, with respect to an axis of the LVOT, adjacent to an aorto-mitral curtain, below a non-coronary cusp (NCC)-left coronary cusp (LCC) interleaflet triangle, and
  - a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and the LCC;
- positioning a second electrode in contact with the left ventricular endocardium of the LVOT at a second-electrode site having:
  - a second-electrode angular location with respect to the axis of the LVOT, the second-electrode angular location different from the first-electrode angular location, and
  - a second-electrode vertical location between the upper plane and the lower plane, the second-electrode vertical location the same as or different from the first-electrode vertical location; and
- activating circuitry to deliver the ventricular pacing pulses by driving a pacing signal between the first and the second electrodes.

For some applications, the first-electrode angular location is adjacent to an aorto-mitral curtain, below a left-lateral end of the NCC.

For some applications, the second-electrode angular location is adjacent to a right fibrous trigone, below the middle of the NCC.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location is adjacent to the left lateral end of the muscular part of a ventricular septum closest to a left fibrous trigone.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location is adjacent to a right side of the muscular part of a ventricular septum, below the RCC.

For some applications:

- the first-electrode angular location is adjacent to an aorto-mitral curtain, below a left-lateral end of the NCC, and
- the second-electrode angular location is adjacent to the muscular part of a ventricular septum, below a mid-portion of the RCC.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location is along adjacent to a right fibrous trigone, below the middle of the NCC.

For some applications, the second-electrode angular location is along adjacent to the left lateral end of the muscular part of a ventricular septum closest to a left fibrous trigone.

There is additionally provided, in accordance with an application of the present invention, a method for delivering ventricular pacing pulses to a heart of a patient, the method including:

- positioning a first electrode in contact with left ventricular endocardium of a left ventricular outflow tract (LVOT) at a first-electrode site having:

a first-electrode angular location, with respect to an axis of the LVOT, adjacent to a left fibrous trigone, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, the second-electrode angular location different from the first-electrode angular location, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

For some applications, the first-electrode angular location is adjacent to an anterior end of the left fibrous trigone and a left lateral end of the muscular part of a ventricular septum.

For some applications, the first-electrode angular location is an aorto-mitral curtain and a posterior end of the left fibrous trigone.

There is yet additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location selected from the group of angular locations consisting of: (a) an angular location, with respect to an axis of the LVOT, adjacent to a right side of the muscular part of a ventricular septum, below a right coronary cusp (RCC), and (b) an angular location, with respect the axis of the LVOT, adjacent to the muscular part of a ventricular septum, below an anterior side of a left coronary cusp (LCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode in contact with the left ventricular endocardium of the LVOT at a second-electrode site having:

a second-electrode angular location with respect to the axis of the LVOT, the second-electrode angular location different from the first-electrode angular location, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

For some applications, the second-electrode angular location is along an angular segment extending, with respect to the axis of the LVOT, inclusively, from (a) adjacent to a right fibrous trigone, below the middle of the NCC, (b) around (i) a portion of the NCC, (ii) the LCC, and (iii) a portion of the RCC, to (c) adjacent to the muscular part of the ventricular septum, anterior to a membranous septum (MS), across from a right ventricular outflow tract. For some of these applications, the second-electrode angular location is selected from the group of angular locations consisting of: (a) an angular location, with respect to an axis of the LVOT, adjacent to the right side of the muscular part of the ventricular septum, below the RCC, and (b) an angular location, with respect the axis of the LVOT, adjacent to the muscular part of a ventricular septum, below the anterior side of the LCC.

For some applications, the first-electrode angular location is adjacent to the right side of the muscular part of the ventricular septum, below the RCC.

For some applications, driving the pacing signal between the first and the second electrodes includes configuring the first and the second electrodes as a cathode and as an anode, respectively.

For some applications, the second-electrode angular location is along an angular segment extending, with respect to the axis of the LVOT, inclusively, from (a) adjacent to a right fibrous trigone, below the middle of the NCC, (b) around (i) a portion of the NCC, (ii) the LCC, and (iii) a portion of the RCC, to (c) adjacent to the muscular part of the ventricular septum, anterior to a membranous septum (MS), across from a right ventricular outflow tract.

For some applications, the first-electrode angular location is adjacent to the muscular part of the ventricular septum, below a left side of the RCC.

For some applications, the second-electrode angular location is adjacent to the muscular part of a ventricular septum, below a right side of the LCC.

For some applications, the first-electrode angular location is adjacent to the muscular part of a ventricular septum, below a mid-portion of the RCC.

For some applications, the second-electrode angular location is selected from the group consisting of: adjacent to the muscular part of the ventricular septum, below a left side of the RCC, and an angular location adjacent to the muscular part of a ventricular septum, below a right side of the LCC.

For some applications, the first-electrode angular location is adjacent to the muscular part of the ventricular septum, anterior to a membranous septum (MS), across from a right ventricular outflow tract.

For some applications, the second-electrode angular location is selected from the group consisting of: adjacent to the muscular part of the ventricular septum, below a left side of the RCC, and an angular location adjacent to the muscular part of a ventricular septum, below a right side of the LCC.

For some applications, the first-electrode angular location is adjacent to the muscular part of the ventricular septum, below the anterior side of the LCC.

For some applications, driving the pacing signal between the first and the second electrodes includes configuring the first and the second electrodes as a cathode and as an anode, respectively.

For some applications, the second-electrode angular location is along an angular segment extending, with respect to the axis of the LVOT, inclusively, from (a) adjacent to a right fibrous trigone, below the middle of the NCC, (b) around (i) a portion of the NCC, (ii) the LCC, and (iii) a portion of the RCC, to (c) adjacent to the muscular part of the ventricular septum, anterior to a membranous septum (MS), across from a right ventricular outflow tract.

For some applications, the first-electrode angular location is adjacent to the left lateral end of the muscular part of a ventricular septum closest to a left fibrous trigone.

For some applications, the first-electrode angular location is adjacent to the muscular part of a ventricular septum, below a right side of the LCC.

There is also provided, in accordance with an application of the present invention, a method for delivering ventricular pacing pulses to a heart of a patient, the method including:

- positioning a first electrode in contact with left ventricular endocardium of a left ventricular outflow tract (LVOT) at a first-electrode site having:
  - a first-electrode angular location, with respect to an axis of the LVOT, adjacent to the muscular part of a ventricular septum, below an anterior side of a left coronary cusp (LCC), and
  - a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and the LCC;
- positioning a second electrode in contact with the left ventricular endocardium of the LVOT at a second-electrode site having:
  - a second-electrode angular location with respect to the axis of the LVOT, the second-electrode angular location different from the first-electrode angular location, and
  - a second-electrode vertical location between the upper plane and the lower plane, the second-electrode vertical location the same as or different from the first-electrode vertical location; and
- activating circuitry to deliver the ventricular pacing pulses by driving a pacing signal between the first and the second electrodes.

For some applications, the first-electrode angular location is adjacent to the left lateral end of the muscular part of a ventricular septum closest to a left fibrous trigone.

For some applications, the second-electrode angular location is adjacent to a right fibrous trigone.

For some applications, the first-electrode angular location is adjacent to the muscular part of a ventricular septum, below a right side of the LCC.

There is further provided, in accordance with an application of the present invention, a method for delivering ventricular pacing pulses to a heart of a patient, the method including:

- positioning a first electrode in contact with left ventricular endocardium of a left ventricular outflow tract (LVOT) at a first-electrode site having:
  - a first-electrode angular location, with respect to an axis of the LVOT, adjacent to a right fibrous trigone, and
  - a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);
- positioning a second electrode in contact with the left ventricular endocardium of the LVOT at a second-electrode site having:
  - a second-electrode angular location with respect to the axis of the LVOT, the second-electrode angular location different from the first-electrode angular location, and
  - a second-electrode vertical location between the upper plane and the lower plane, the second-electrode vertical location the same as or different from the first-electrode vertical location; and
- activating circuitry to deliver the ventricular pacing pulses by driving a pacing signal between the first and the second electrodes.

For some applications, the first-electrode angular location is adjacent to the right fibrous trigone, below the middle of the NCC.

For some applications, the second-electrode angular location is adjacent to the muscular part of a ventricular septum, below an anterior side of the LCC.

For some applications, the second-electrode angular location is adjacent to the left lateral end of the muscular part of a ventricular septum closest to a left fibrous trigone.

There is still further provided, in accordance with an application of the present invention, a method for delivering ventricular pacing pulses to a heart of a patient, the method including:

- positioning a first electrode in contact with left ventricular endocardium of a left ventricular outflow tract (LVOT) at a first-electrode site having:
  - a first-electrode angular location, with respect to an axis of the LVOT, adjacent to a right fibrous trigone, below the middle of a non-coronary cusp (NCC), and
  - a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);
- positioning a second electrode in contact with the left ventricular endocardium of the LVOT at a second-electrode site having:
  - a second-electrode angular location, with respect to the axis of the LVOT, adjacent to the left lateral end of the muscular part of a ventricular septum closest to a left fibrous trigone, and
  - a second-electrode vertical location between the upper plane and the lower plane, the second-electrode vertical location the same as or different from the first-electrode vertical location; and
- activating circuitry to deliver the ventricular pacing pulses by driving a pacing signal between the first and the second electrodes.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

There is additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location, with respect to the axis of the LVOT, adjacent to a membranous septum, below a right lateral end of the RCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

For some applications, driving the pacing signal between the first and the second electrodes includes configuring the first and the second electrodes as a cathode and as an anode, respectively.

For some applications, driving the pacing signal between the first and the second electrodes includes configuring the first and the second electrodes as an anode and as a cathode, respectively.

There is yet additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to an anterior end of a left fibrous trigone and a left lateral end of the muscular part of a ventricular septum, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is also provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to a membranous septum, below a right lateral end of the RCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to an aorto-mitral curtain and a posterior end of a left fibrous trigone, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is still further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to an anterior end of a left fibrous trigone and a left lateral end of the muscular part of a ventricular septum, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to a membranous septum, below a right lateral end of the RCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a right coronary cusp (RCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode in contact with the left ventricular endocardium of the LVOT at a second-electrode site having:

a second-electrode angular location with respect to the axis of the LVOT, adjacent to a right fibrous trigone, below the middle of the NCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is yet additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a right coronary cusp (RCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode in contact with the left ventricular endocardium of the LVOT at a second-electrode site having:

a second-electrode angular location with respect to the axis of the LVOT, adjacent to an aorto-mitral curtain, below a left-lateral end of the NCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is also provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a right coronary cusp (RCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode in contact with the left ventricular endocardium of the LVOT at a second-electrode site having:

a second-electrode angular location with respect to the axis of the LVOT, adjacent to the left lateral end of the muscular part of a ventricular septum closest to a left fibrous trigone, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a right coronary cusp (RCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode in contact with the left ventricular endocardium of the LVOT at a second-electrode site having:

a second-electrode angular location with respect to the axis of the LVOT, adjacent to an aorto-mitral curtain and a posterior end of a left fibrous trigone, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is still further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a right fibrous trigone, below the middle of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to an aorto-mitral curtain, below a left-lateral end of the NCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a right fibrous trigone, below the middle of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to the left lateral end of the muscular part of a ventricular septum closest to a left fibrous trigone, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is yet additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to an aorto-mitral curtain, below a left-lateral end of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to the left lateral end of the muscular part of a ventricular septum closest to a left fibrous trigone, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is also provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to an aorto-mitral curtain, below a left-lateral end of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to the muscular part of a ventricular septum, below a mid-portion of the RCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

There is further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to the left lateral end of the muscular part of a ventricular septum closest to a left fibrous trigone, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, adjacent to the muscular part of a ventricular septum, below a mid-portion of the RCC, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

For some applications, the second-electrode vertical location is the same as the first-electrode vertical location.

For some applications, positioning the first electrode at the first-electrode site and positioning the second electrode at the second-electrode site include:

delivering a frame to an aortic position in the heart in a constrained delivery configuration, the frame including interconnected stent struts, wherein the first and the second electrodes are coupled to the frame; and transitioning the frame to an expanded deployment configuration, in which the frame positions and holds the first and the second electrodes in contact with the left ventricular endocardium of the LVOT at the first-electrode and the second-electrode sites, respectively.

For some applications, delivering the frame includes delivering a prosthetic aortic valve to the native aortic valve, the prosthetic aortic valve including the frame and a plurality of prosthetic leaflets coupled to the frame so as to allow blood flow in a downstream direction and inhibit blood flow in an upstream direction.

For some applications, positioning the first electrode at the first-electrode site and positioning the second electrode at the second-electrode site include:

delivering a support to an aortic position in the heart in a constrained delivery configuration, wherein the first and the second electrodes are coupled to the support; and transitioning the support to an expanded deployment configuration, in which the support positions and holds the first and the second electrodes in contact with the left ventricular endocardium of the LVOT at the first-electrode and the second-electrode sites, respectively.

For some applications, the method further includes introducing a prosthetic aortic valve into a body of the patient and placing the prosthetic aortic valve within the support, the prosthetic aortic valve including a plurality of prosthetic leaflets arranged so as to allow blood flow in a downstream direction and inhibit blood flow in an upstream direction.

For some applications, activating the circuitry includes activating the circuitry to deliver the ventricular pacing pulses includes applying each of the pulses with a voltage of no more than 25 V.

For some applications, the voltage is no more than 12 V.

For some applications, activating the circuitry includes activating the circuitry to deliver the ventricular pacing pulses includes applying each of the pulses with a pulse duration of no more than 0.7 milliseconds.

For some applications, activating the circuitry includes activating the circuitry to deliver the ventricular pacing pulses includes applying each of the pulses with an amplitude of no more than 50 milliamps.

For some applications, activating the circuitry includes activating the circuitry to deliver the ventricular pacing pulses includes applying each of the pulses with a pulse duration of no more than 0.7 milliseconds.

For some applications, activating the circuitry includes activating the circuitry to deliver the ventricular pacing pulses includes configuring the first electrode as an anode and the second electrode a cathode.

For some applications, activating the circuitry includes activating the circuitry to deliver the ventricular pacing pulses includes configuring the first electrode as a cathode and the second electrode an anode.

There is still further provided, in accordance with an application of the present invention, a method for delivering ventricular pacing pulses to a heart of a patient, the method including:

positioning a first electrode at a first-electrode site in contact with tissue of an interleaflet triangle of a native aortic valve;

positioning a second electrode at a second-electrode site in electrical communication with a body of the patient; and activating circuitry to deliver the ventricular pacing pulses by driving a pacing signal between the first and the second electrodes.

For some applications, the first-electrode site is closer to an aortic annulus plane than to a plane defined by respective commissures of a non-coronary cusp (NCC), a right coronary cusp (RCC), and a left coronary cusp (LCC) of the native aortic valve, and the aortic annulus plane is the plane defined by respective nadirs of the NCC, the RCC, and the LCC.

For some applications, the second-electrode site is in the aorta, and positioning the second electrode includes positioning the second electrode at the second-electrode site in the aorta.

For some applications, positioning the second electrode includes positioning the second electrode at the second-electrode site in the aorta angularly aligned with first-electrode site.

For some applications:

the interleaflet triangle is a first interleaflet triangle, and positioning the second electrode includes positioning the second electrode at the second-electrode site in contact with tissue of a second interleaflet triangle of the aortic valve.

For some applications, positioning the second electrode within the patient's body includes positioning the second electrode in contact with left ventricular endocardium of a left ventricular outflow tract (LVOT) at the second-electrode site, the second-electrode site has a vertical location between (a) an upper plane corresponding to an aortic annulus plane and (b) a lower plane parallel to and at a distance below the aortic annulus plane, the distance equal to 8% of a perimeter of an aortic annulus, and the aortic annulus plane is the plane defined by respective nadirs of the NCC, the RCC, and the LCC.

For some applications, activating the circuitry includes activating the circuitry to deliver the ventricular pacing pulses includes applying each of the pulses with a voltage of no more than 25 V.

For some applications, activating the circuitry includes activating the circuitry to deliver the ventricular pacing pulses includes applying each of the pulses with a pulse duration of no more than 0.7 milliseconds.

For some applications, activating the circuitry includes activating the circuitry to deliver the ventricular pacing pulses includes applying each of the pulses with an amplitude of no more than 50 milliamps.

For some applications, activating the circuitry includes activating the circuitry to deliver the ventricular pacing pulses includes applying each of the pulses with a pulse duration of no more than 0.7 milliseconds.

For some applications, activating the circuitry includes activating the circuitry to deliver the ventricular pacing pulses includes configuring the first electrode as an anode and the second electrode a cathode.

For some applications, activating the circuitry includes activating the circuitry to deliver the ventricular pacing pulses includes configuring the first electrode as a cathode and the second electrode an anode.

For some applications, positioning the first electrode at the first-electrode site includes:

delivering a frame to an aortic position in the heart in a constrained delivery configuration, the frame including interconnected stent struts, wherein the first electrode is coupled to the frame; and transitioning the frame to an expanded deployment configuration, in which the frame positions and holds the first electrode in contact with the tissue of the interleaflet triangle.

For some applications, delivering the frame includes delivering a prosthetic aortic valve to the native aortic valve, the prosthetic aortic valve including the frame and a plurality of prosthetic leaflets coupled to the frame so as to allow blood flow in a downstream direction and inhibit blood flow in an upstream direction.

There is additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to a membranous septum, below a right lateral end of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode at a second-electrode site in electrical communication with a body of the patient; and activating circuitry to deliver the ventricular pacing pulses by driving a pacing signal between the first and the second electrodes.

There is yet additionally provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to the axis of the LVOT, adjacent to an aorto-mitral curtain, below a non-coronary cusp (NCC)-left coronary cusp (LCC) interleaflet triangle, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and the LCC;

positioning a second electrode at a second-electrode site in electrical communication with a body of the patient; and activating the circuitry includes activating the circuitry to deliver the ventricular pacing pulses by driving a pacing signal between the first and the second electrodes.

There is also provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to the muscular part of a ventricular septum, anterior to a membranous septum, across from a right ventricular outflow tract (RVOT), below the middle of a right coronary cusp (RCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode at a second-electrode site in electrical communication with a body of the patient; and activating the circuitry includes activating the circuitry to deliver the ventricular pacing pulses by driving a pacing signal between the first and the second electrodes.

There is further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to the axis of the LVOT, adjacent to a right fibrous trigone, below the middle of a non-coronary cusp (NCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode at a second-electrode site in electrical communication with a body of the patient; and activating the circuitry includes activating the circuitry to deliver the ventricular pacing pulses by driving a pacing signal between the first and the second electrodes.

There is still further provided, in accordance with an application of the present invention, a method for delivering ventricular pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, adjacent to the left lateral end of the muscular part of a ventricular septum closest to a left fibrous trigone, and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);

positioning a second electrode at a second-electrode site in electrical communication with a body of the patient; and activating the circuitry includes activating the circuitry to deliver the ventricular pacing pulses by driving a pacing signal between the first and the second electrodes.

For some applications, positioning the second electrode at the second-electrode site includes positioning the second electrode in the patient's body.

For some applications, positioning the second electrode at the second-electrode site includes positioning the second electrode in the aorta.

For some applications, positioning the second electrode at the second-electrode site includes positioning the second electrode in the aorta angularly aligned with the first-electrode angular location.

For some applications, positioning the second electrode at the second-electrode site includes positioning the second electrode in contact with blood and not in contact with an aortic wall.

For some applications, positioning the first electrode at the first-electrode site includes:

delivering a frame to an aortic position in the heart in a constrained delivery configuration, the frame including interconnected stent struts, wherein the first electrode is coupled to the frame; and transitioning the frame to an expanded deployment configuration, in which the frame positions and holds the first electrode in contact with the left ventricular endocardium of the LVOT at the first-electrode site.

For some applications:

the second electrode is coupled to the frame, and positioning the second electrode at the second-electrode site includes transitioning the frame to the expanded deployment configuration, in which the frame positions and holds the second electrode at the second-electrode site.

For some applications, delivering the frame includes delivering a prosthetic aortic valve to the native aortic valve, the prosthetic aortic valve including the frame and a plurality of prosthetic leaflets coupled to the frame so as to allow blood flow in a downstream direction and inhibit blood flow in an upstream direction.

For some applications, activating the circuitry includes activating the circuitry to deliver the ventricular pacing pulses includes applying each of the pulses with a voltage of no more than 25 V.

For some applications, activating the circuitry includes activating the circuitry to deliver the ventricular pacing pulses includes applying each of the pulses with a pulse duration of no more than 0.7 milliseconds.

For some applications, activating the circuitry includes activating the circuitry to deliver the ventricular pacing pulses includes applying each of the pulses with an amplitude of no more than 50 milliamps.

For some applications, activating the circuitry includes activating the circuitry to deliver the ventricular pacing pulses includes applying each of the pulses with a pulse duration of no more than 0.7 milliseconds.

For some applications, activating the circuitry includes activating the circuitry to deliver the ventricular pacing pulses includes configuring the first electrode as an anode and the second electrode a cathode.

For some applications, activating the circuitry includes activating the circuitry to deliver the ventricular pacing pulses includes configuring the first electrode as a cathode and the second electrode an anode.

There is additionally provided, in accordance with an application of the present invention, a method for sensing electrical activity a heart of a patient, the method including:

- positioning a first electrode in contact with left ventricular endocardium of a left ventricular outflow tract (LVOT) at a first-electrode site having:
  - a first-electrode angular location, with respect to an axis of the LVOT, along a partially anterior angular segment extending, with respect to the axis of the LVOT, inclusively, from (a) a posterior end of a membranous septum (MS), (b) around an anterior portion of the LVOT, to (c) an anterior end of a left fibrous trigone (LFT); and
  - a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), a right coronary cusp (RCC), and a left coronary cusp (LCC);
- positioning a second electrode in contact with the left ventricular endocardium of the LVOT at a second-electrode site having:
  - a second-electrode angular location, with respect to the axis of the LVOT, along the partially anterior angular segment, the second-electrode angular location different from the first-electrode angular location, and
  - a second-electrode vertical location between the upper plane and the lower plane, the second-electrode vertical location the same as or different from the first-electrode vertical location; and
- activating circuitry to attempt to identify an intrinsic ventricular activation signal in an intracardiac electrogram (EGM) sensed using the first and the second electrodes.

For some applications, the first-electrode angular location is along a sub-segment of the partially anterior angular segment, the sub-segment extending, with respect to the axis of the LVOT, inclusively, from (a) adjacent to the membranous septum, below a right lateral end of the NCC, (b) around the anterior portion of the LVOT, to (c) the anterior end of the LFT.

For some applications, the first-electrode angular location is along a sub-segment of the partially anterior angular segment, the sub-segment extending, with respect to the axis of the LVOT, inclusively, from (a) the posterior end of the MS, (b) around the anterior portion of the LVOT, to (c) adjacent to the left lateral end of the muscular part of the ventricular septum closest to the LFT.

For some applications, the first-electrode angular location is along a sub-segment of the partially anterior angular segment, the sub-segment extending, with respect to the axis of the LVOT, inclusively, from (a) adjacent to the membranous septum, below a right lateral end of the NCC, (b) around the anterior portion of the LVOT, to (c) adjacent to the left lateral end of the muscular part of the ventricular septum closest to the LFT.

For some applications, the second-electrode angular location is offset from the first-electrode angular location by at least 10 degrees with respect to the axis of the LVOT.

For some applications, the first-electrode angular location is adjacent to the left lateral end of the muscular part of a ventricular septum closest to a left fibrous trigone.

For some applications, the second-electrode angular location is adjacent to the muscular part of a ventricular septum, below a left side of the RCC.

For some applications, the second-electrode angular location is adjacent to the muscular part of a ventricular septum, below a mid-portion of the RCC.

For some applications, the second-electrode angular location is adjacent to a membranous septum, below a right lateral end of the NCC.

For some applications, the first-electrode angular location is adjacent to the muscular part of a ventricular septum, below a left side of the RCC.

For some applications, the second-electrode angular location is adjacent to a membranous septum, below a right lateral end of the NCC.

For some applications, the second-electrode angular location is adjacent to a membranous septum, below a right lateral end of the RCC.

For some applications, the first-electrode angular location is adjacent to the muscular part of a ventricular septum, below a mid-portion of the RCC.

For some applications, the first-electrode angular location is adjacent to a membranous septum, below a right lateral end of the NCC.

For some applications, the first-electrode angular location is adjacent to a membranous septum, below a right lateral end of the RCC.

There is yet additionally provided, in accordance with an application of the present invention, a method for sensing electrical activity a heart of a patient, the method including:

- positioning a first electrode in contact with left ventricular endocardium of a left ventricular outflow tract (LVOT) at a first-electrode site having:
  - a first-electrode angular location, with respect to an axis of the LVOT, along a partially left angular segment extending, with respect to the axis of the LVOT, inclusively, from (a) adjacent to an anterior end of a left fibrous trigone (LFT) and a left lateral end of the muscular part of a ventricular septum, (b) around a left posterior portion of the LVOT, to (c) below a middle of a non-coronary cusp (NCC); and
  - a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);
- positioning a second electrode in contact with the left ventricular endocardium of the LVOT at a second-electrode site having:
  - a second-electrode angular location, with respect to the axis of the LVOT, along the partially left angular segment, the second-electrode angular location different from the first-electrode angular location, and
  - a second-electrode vertical location between the upper plane and the lower plane, the second-electrode vertical location the same as or different from the first-electrode vertical location; and activating circuitry to attempt to identify an intrinsic ventricular activation signal in an intracardiac electrogram (EGM) sensed using the first and the second electrodes.

For some applications, the second-electrode angular location is offset from the first-electrode angular location by at least 10 degrees with respect to the axis of the LVOT.

For some applications, the first-electrode angular location is adjacent to an anterior end of the left fibrous trigone and a left lateral end of the muscular part of a ventricular septum.

For some applications, the second-electrode angular location is adjacent to an aorto-mitral curtain and a posterior end of the left fibrous trigone.

For some applications, the first-electrode angular location is adjacent to an aorto-mitral curtain and a posterior end of the left fibrous trigone.

For some applications, the second-electrode angular location is below the middle of the NCC.

For some applications, the first-electrode angular location is below the middle of the NCC.

There is also provided, in accordance with an application of the present invention, a method for sensing electrical activity a heart of a patient, the method including:

positioning a first electrode in contact with left ventricular endocardium of a left ventricular outflow tract (LVOT) at a first-electrode site having:

a first-electrode angular location, with respect to an axis of the LVOT, (a) adjacent to a right side of the muscular part of a ventricular septum, below a right coronary cusp (RCC), (b) adjacent to the muscular part of a ventricular septum, below an anterior side of a left coronary cusp (LCC), or (c) adjacent to a membranous septum; and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and the LCC;

positioning a second electrode in contact with the left ventricular endocardium of the LVOT at a second-electrode site having:

a second-electrode angular location, with respect to the axis of the LVOT, along the partially left angular segment, the second-electrode angular location different from the first-electrode angular location, and a second-electrode vertical location between the upper plane and the lower plane, the second-electrode vertical location the same as or different from the first-electrode vertical location; and activating circuitry to attempt to identify an intrinsic ventricular activation signal in an intracardiac electrogram (EGM) sensed using the first and the second electrodes.

For some applications, the first-electrode angular location is adjacent to the right side of the muscular part of the ventricular septum, below the RCC.

For some applications, the first-electrode angular location is adjacent to the muscular part of the ventricular septum, below a left side of the RCC.

For some applications, the first-electrode angular location is adjacent to the muscular part of a ventricular septum, below a mid-portion of the RCC.

For some applications, the first-electrode angular location is adjacent to the muscular part of the ventricular septum, below the anterior side of the LCC.

For some applications, the first-electrode angular location is adjacent to the muscular part of a ventricular septum, below a right side of the LCC.

For some applications, the first-electrode angular location is adjacent to the membranous septum.

For some applications, activating the circuitry includes activating the circuitry to attempt to identify the intrinsic ventricular activation signal in the intracardiac EGM by sensing using only the first and the second electrodes.

For some applications, activating the circuitry includes activating the circuitry to attempt to identify the intrinsic ventricular activation signal in the intracardiac EGM by configuring the first and the second electrodes as a cathode and as an anode, respectively.

For some applications, activating the circuitry includes activating the circuitry to attempt to identify the intrinsic ventricular activation signal in the intracardiac EGM by configuring the first and the second electrodes as an anode and as a cathode, respectively.

For some applications, the second-electrode vertical location is the same as the first-electrode vertical location.

For some applications, positioning the first electrode at the first-electrode site and positioning the second electrode at the second-electrode site include:

delivering a frame to an aortic position in the heart in a constrained delivery configuration, the frame including interconnected stent struts, wherein the first and the second electrodes are coupled to the frame; and transitioning the frame to an expanded deployment configuration, in which the frame positions and holds the first and the second electrodes in contact with the left ventricular endocardium of the LVOT at the first-electrode and the second-electrode sites, respectively.

For some applications, delivering the frame includes delivering a prosthetic aortic valve to the native aortic valve, the prosthetic aortic valve including the frame and a plurality of prosthetic leaflets coupled to the frame so as to allow blood flow in a downstream direction and inhibit blood flow in an upstream direction.

For some applications, positioning the first electrode at the first-electrode site and positioning the second electrode at the second-electrode site include:

delivering a support to an aortic position in the heart in a constrained delivery configuration, wherein the first and the second electrodes are coupled to the support; and transitioning the support to an expanded deployment configuration, in which the support positions and holds the first and the second electrodes in contact with the left ventricular endocardium of the LVOT at the first-electrode and the second-electrode sites, respectively.

For some applications, the method further includes introducing a prosthetic aortic valve into a body of the patient and placing the prosthetic aortic valve within the support, the prosthetic aortic valve including a plurality of prosthetic leaflets arranged so as to allow blood flow in a downstream direction and inhibit blood flow in an upstream direction.

There is further provided, in accordance with an application of the present invention, a method for sensing electrical activity a heart of a patient, the method including:

positioning a first electrode in contact with left ventricular endocardium of a left ventricular outflow tract (LVOT) at a first-electrode site having:

a first-electrode angular location, with respect to an axis of the LVOT, along an angular segment extending, with respect to the axis of the LVOT, inclusively, from (a) adjacent to an anterior end of a left fibrous trigone (LFT) and a left lateral end of the muscular part of a ventricular septum, (b) around a posterior portion of the LVOT, to (c) adjacent to a membranous septum (MS), below a right lateral end of a right coronary cusp (RCC); and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and a left coronary cusp (LCC);

positioning a second electrode in contact with the left ventricular endocardium of the LVOT at a second-electrode site having:

a second-electrode angular location, with respect to the axis of the LVOT, along the partially left angular segment, the second-electrode angular location different from the first-electrode angular location, and a second-electrode vertical location between the upper plane and the lower plane, the second-electrode vertical location the same as or different from the first-electrode vertical location; and activating circuitry to attempt to identify an intrinsic atrial activation signal in an intracardiac electrogram (EGM) sensed using the first and the second electrodes.

For some applications, the first-electrode angular location is adjacent to a right fibrous trigone.

For some applications, the first-electrode angular location is adjacent to a mid-portion of the NCC, closer to an NCC-LCC commissure than to an NCC-RCC commissure.

For some applications, the first-electrode angular location is adjacent to the right fibrous trigone, below the middle of the NCC.

For some applications, the first-electrode angular location is adjacent to an aorto-mitral curtain, below an NCC-LCC interleaflet triangle.

For some applications, the first-electrode angular location is adjacent to an aorto-mitral curtain, below a left-lateral end of the NCC.

For some applications, the first-electrode angular location is adjacent to the left fibrous trigone.

For some applications, the first-electrode angular location is adjacent to an aorto-mitral curtain and a posterior end of the left fibrous trigone.

For some applications, activating the circuitry includes activating the circuitry to attempt to identify the intrinsic atrial activation signal in the intracardiac EGM by sensing using only the first and the second electrodes.

For some applications, activating the circuitry includes activating the circuitry to attempt to identify the intrinsic atrial activation signal in the intracardiac EGM by configuring the first and the second electrodes as a cathode and as an anode, respectively.

For some applications, activating the circuitry includes activating the circuitry to attempt to identify the intrinsic atrial activation signal in the intracardiac EGM by configuring the first and the second electrodes as an anode and as a cathode, respectively.

There is still further provided, in accordance with an application of the present invention, a method for delivering atrial pacing pulses to a heart of a patient, the method including:

positioning a first electrode in contact with left ventricular endocardium of a left ventricular outflow tract (LVOT) at a first-electrode site having:

a first-electrode angular location, with respect to an axis of the LVOT, along a partially left angular segment extending, with respect to the axis of the LVOT, inclusively, from (a) adjacent to an anterior end of a left fibrous trigone and a left lateral end of the muscular part of a ventricular septum, (b) around a left posterior portion of the LVOT, to (c) below a middle of a non-coronary cusp (NCC); and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of the NCC, a right coronary cusp (RCC), and a left coronary cusp (LCC);

positioning a second electrode in contact with the left ventricular endocardium of the LVOT at a second-electrode site having:

a second-electrode angular location with respect to the axis of the LVOT, the second-electrode angular location different from the first-electrode angular location, and a second-electrode vertical location between the upper plane and the lower plane, the second-electrode vertical location the same as or different from the first-electrode vertical location; and activating circuitry to deliver the atrial pacing pulses by driving a pacing signal between the first and the second electrodes.

For some applications, the first-electrode angular location is adjacent to the left fibrous trigone.

For some applications, the first-electrode angular location is adjacent to an aorto-mitral curtain and a posterior end of the left fibrous trigone.

For some applications, the first-electrode angular location is adjacent to an aorto-mitral curtain, below an NCC-LCC interleaflet triangle.

For some applications, the first-electrode angular location is adjacent to an aorto-mitral curtain, below a left-lateral end of the NCC.

For some applications, activating the circuitry includes activating the circuitry to deliver the atrial pacing pulses includes configuring the first electrode as a cathode and the second electrode an anode.

For some applications, activating the circuitry includes activating the circuitry to deliver the atrial pacing pulses includes configuring the first electrode as an anode and the second electrode a cathode.

For some applications, the first-electrode angular location is along an angular segment extending, with respect to the axis of the LVOT, inclusively, from (a) adjacent to the aorto-mitral curtain, below the left-lateral end of the NCC to (b) adjacent to the mid-portion of the NCC, closer to the NCC-LCC commissure than to the NCC-RCC commissure.

For some applications, activating the circuitry includes activating the circuitry to deliver the atrial pacing pulses includes configuring the first electrode as a cathode and the second electrode an anode.

For some applications, activating the circuitry includes activating the circuitry to deliver the atrial pacing pulses includes configuring the first electrode as a cathode and the second electrode an anode.

For some applications, the first-electrode angular location is adjacent to a right fibrous trigone.

For some applications, the first-electrode angular location is adjacent to a mid-portion of the NCC, closer to an NCC-LCC commissure than to an NCC-RCC commissure.

For some applications, activating the circuitry includes activating the circuitry to deliver the atrial pacing pulses includes configuring the first electrode as a cathode and the second electrode an anode.

For some applications, activating the circuitry includes activating the circuitry to deliver the atrial pacing pulses includes configuring the first electrode as an anode and the second electrode a cathode.

For some applications, the first-electrode angular location is adjacent to the right fibrous trigone, below the middle of the NCC.

For some applications, activating the circuitry includes activating the circuitry to deliver the atrial pacing pulses includes configuring the first electrode as an anode and the second electrode a cathode.

For some applications, activating the circuitry includes activating the circuitry to deliver the atrial pacing pulses includes configuring the first electrode as an anode and the second electrode a cathode.

For some applications, the second-electrode vertical location is the same as the first-electrode vertical location.

For some applications, positioning the first electrode at the first-electrode site and positioning the second electrode at the second-electrode site include:

- delivering a frame to an aortic position in the heart in a constrained delivery configuration, the frame including interconnected stent struts, wherein the first and the second electrodes are coupled to the frame; and
- transitioning the frame to an expanded deployment configuration, in which the frame positions and holds the first and the second electrodes in contact with the left ventricular endocardium of the LVOT at the first-electrode and the second-electrode sites, respectively.

For some applications, delivering the frame includes delivering a prosthetic aortic valve to the native aortic valve, the prosthetic aortic valve including the frame and a plurality of prosthetic leaflets coupled to the frame so as to allow blood flow in a downstream direction and inhibit blood flow in an upstream direction.

For some applications, positioning the first electrode at the first-electrode site and positioning the second electrode at the second-electrode site include:

- delivering a support to an aortic position in the heart in a constrained delivery configuration, wherein the first and the second electrodes are coupled to the support; and
- transitioning the support to an expanded deployment configuration, in which the support positions and holds the first and the second electrodes in contact with the left ventricular endocardium of the LVOT at the first-electrode and the second-electrode sites, respectively.

For some applications, the method further includes introducing a prosthetic aortic valve into a body of the patient and placing the prosthetic aortic valve within the support, the prosthetic aortic valve including a plurality of prosthetic leaflets arranged so as to allow blood flow in a downstream direction and inhibit blood flow in an upstream direction.

The present invention will be more fully understood from the following detailed description of embodiments thereof, taken together with the drawings, in which:

DETAILED DESCRIPTION OF APPLICATIONS

Figure 1:
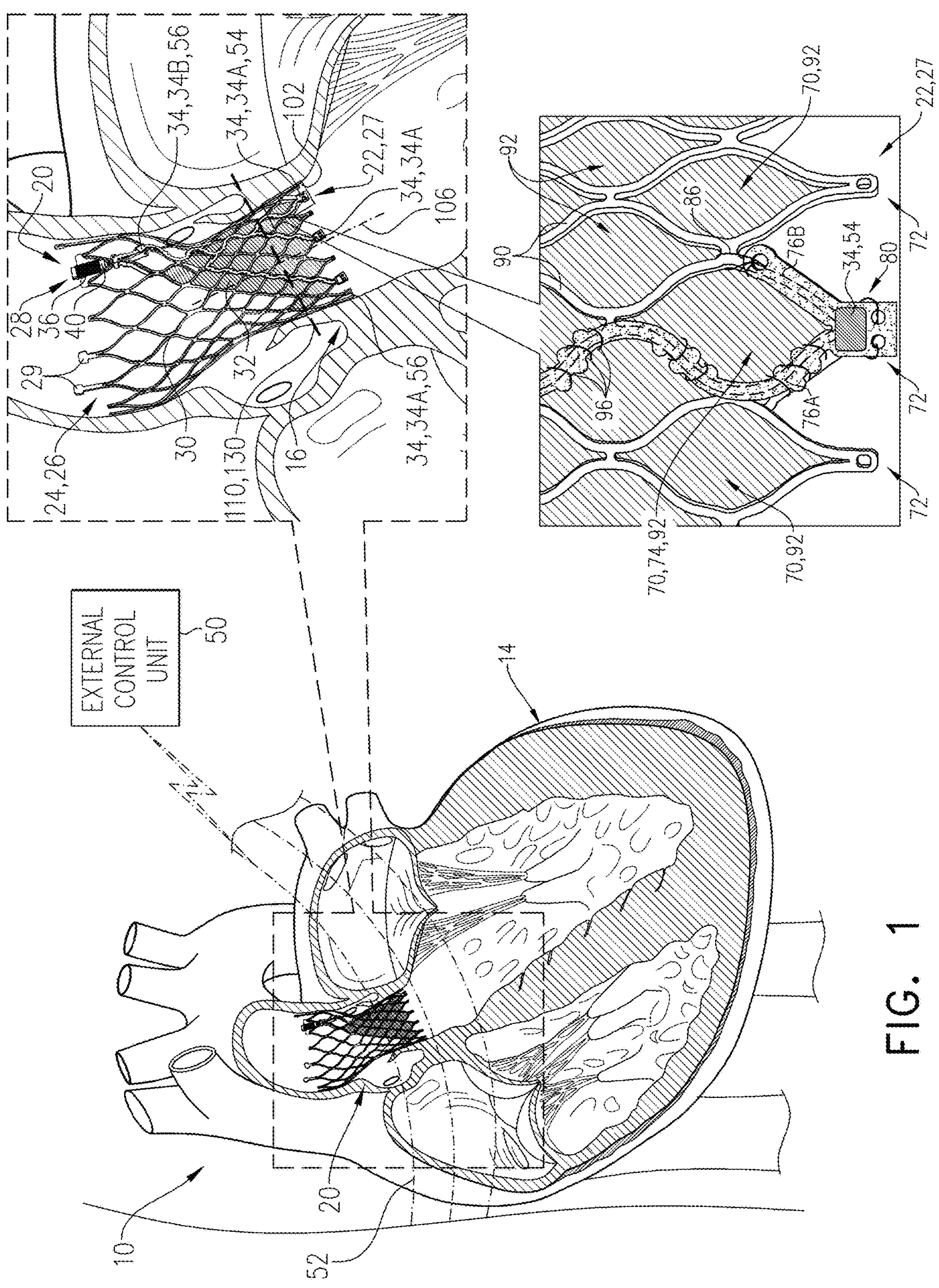
FIG. 1 is a schematic illustration of a prosthetic cardiac valve system applied to a body of a patient, in accordance with an application of the present invention.

Reference is made to FIG. 1, which is a schematic illustration of a prosthetic cardiac valve system 10 applied to a body of a patient, in accordance with an application of the present invention. For some applications, prosthetic cardiac valve system 10 comprises a prosthetic aortic valve 20 configured to be implanted in the patient's body. Prosthetic aortic valve 20 is shown in FIG. 1 implanted in the patient's body in an expanded configuration.

Prosthetic aortic valve 20 has an upstream end 22 and a downstream end 24. Downstream end 24 may also be a proximal end 26 and upstream end 22 may also be a distal end 27, for example because proximal end 26 may be disposed in a distal end portion of a delivery sheath more proximally than distal end 27; in other words, proximal end 26 is closer to a proximal end portion of the delivery sheath than is distal end 27. Prosthetic aortic valve 20 comprises:

- a frame 30;
- a plurality of prosthetic leaflets 32 coupled to frame 30 so as to allow blood flow in a proximal downstream direction and inhibit blood flow in an upstream direction when prosthetic aortic valve 20 is in the expanded deployment configuration, such as shown in FIG. 1;
- optionally, an antenna 28, which is mechanically coupled to frame 30, and which comprises one or more prosthetic-valve coils 36;
- one or more electrodes 34, such as a cathode 54 and an anode 56, coupled to frame 30; and
- optionally, circuitry 40, which is electrically coupled to the one or more electrodes 34 and the one or more prosthetic-valve coils 36.

Typically, the one or more electrodes 34 include at least a first electrode 34A, which is disposed at a distal upstream portion of prosthetic aortic valve 20, such as a distal upstream half, e.g., a distal upstream third, such as a distal upstream quarter, of prosthetic aortic valve 20. First electrode 34A may be configured as a cathode 54 (such as shown), or as an anode 56 (configuration not shown). Optionally, the one or more electrodes 34 include two or more first electrodes 34A (e.g., three or more first electrodes 34A, such as three first electrodes 34A, as shown by way of example and not limitation), which are disposed at a distal upstream portion of prosthetic aortic valve 20, such as a distal upstream half, e.g., a distal upstream third, such as a distal upstream quarter, of prosthetic aortic valve 20. At least one of first electrodes 34A may be configured as a cathode 54, and at least another of first electrodes 34A may be configured as an anode 56 (such as shown).

Optionally, the one or more electrodes 34 include a second electrode 34B, which is disposed at a proximal downstream portion of prosthetic aortic valve 20, such as a proximal downstream half, e.g., a proximal downstream third, such as a proximal downstream quarter, of prosthetic aortic valve 20.

Prosthetic aortic valve 20 is typically configured to be delivered, in a constrained delivery configuration within a delivery sheath, to an aortic position in the heart of the patient (either to a native aortic valve 16 or a previously implanted prosthetic aortic valve for TAVI-in-TAV). Typically, prosthetic aortic valve 20 is deployed using imaging, such as fluoroscopy, and is rotated and/or axially moved if necessary during the deployment in order to achieve the desired location(s) of at least one of the one or more electrodes 34, such as described in detail hereinbelow. For some applications, such as shown, proximal end 26 is configured to be coupled to a delivery system (e.g., shaped so as to define delivery-tool-coupling tabs 29, which are configured to removably couple frame 30, and thus prosthetic aortic valve 20, to the delivery system, e.g., to a delivery shaft of the delivery system). For other applications (configuration not shown), distal end 27 is configured to be coupled to the delivery system, such as to a capsule of a distal end portion of a delivery sheath.

Reference is still made to FIG. 1. Typically, circuitry 40 is configured to apply pacing to a heart 14 using the one or more electrodes 34. For example, the pacing may be applied temporarily for up to several months after implantation of prosthetic aortic valve 20, typically using an external control unit to continuously provide power, such as external control unit 50, described hereinbelow. Alternatively, for some applications, the pacing is applied longer-term, in which case: (a) prosthetic aortic valve 20 may further comprise an energy storage module, e.g., comprising a battery, which may be periodically charged using the external control unit, which may obviate the need for the patient to constantly wear an external energy transmitter, or (b) prosthetic cardiac valve system 10 may comprise one or more subcutaneous energy modules that are configured to transmit the energy to prosthetic aortic valve 20, instead of an integrated battery in the valve. For example, the pacing may comprise ongoing sensing of a native electrical signal of heart 14 and deliverance of electrical stimulus in cases in which the native signal is unsatisfactory for timely ventricular contraction ("VVI pacing"). Further alternatively or additionally, for some applications, circuitry 40 is configured to apply rapid pacing during an invasive structural heart procedure, such as an implantation procedure, such as TAVR.

For some applications, prosthetic aortic valve 20 is configured to sense an electrocardiogramand/or an intracardiac electrogram (EGM) of the patient's heart 14. Circuitry 40 may be configured to sense the ECG and/or EGM, or separate circuitry may be provided for sensing the ECG and/or EGM. The EGM sensing may be performed using all or a subset of electrodes 34 and/or one or more separate electrodes may be provided for performing the EGM sensing. Optionally, the EGM is sensed using techniques described hereinbelow with reference to FIGS. 6A-7E.

Frame 30 typically comprises a stent or other structure, which is typically self-expanding, and may be formed by laser cutting or etching a metal alloy tube comprising, for example, stainless steel, cobalt chrome, or a shape memory material such as Nitinol. For some applications, frame 30 comprises interconnected stent struts 90 arranged so as to define interconnected stent cells 92. Optionally, interconnected stent cells 92 are generally diamond-shaped, such as shown in FIG. 1.

Typically, adjoining pairs of prosthetic leaflets 32 are attached to one another at their lateral ends to form commissures, with free edges of the prosthetic leaflets forming coaptation edges that meet one another. Prosthetic leaflets 32 typically comprise a sheet of animal pericardial tissue, such as porcine pericardial tissue, or synthetic or polymeric material. Optionally, prosthetic aortic valve 20 further comprises a skirt.

For some applications, such as shown in FIG. 1, distal upstream ones 70 of interconnected stent cells 92 are located in a distal upstream half of frame 30 and define respective distal upstream peaks 72. At least one electrode 34, such as a cathode 54 (as labeled) or an anode 56 (configuration not labeled), is disposed at or near (e.g., within 8 mm of) a distal upstream peak 72 of one 74 of the distal upstream stent cells 70 (and is thus referred to herein as a distal upstream electrode 34). First and second distal upstream stent struts 76A and 76B of the one 74 of distal upstream stent cells 70 are joined at the distal upstream peak 72 (the distal upstream peak 72 is obscured in FIG. 3D, but can be seen in the adjacent stent cells). Optionally, such as shown, the distal upstream ones 70 of stent cells 92 are distal upstream-most ones of stent cells 92, and the one 74 of distal upstream stent cells 70 is one 74 of distal upstream-most stent cells 92.

For some applications, cathode 54 has a thickness of at least 10 microns, no more than 200 microns, and/or between 10 and 200 microns, e.g., about 50 microns, and/or a surface area of at least 0.5 $mm^2$, e.g., at least 1 $mm^2$; no more than 20 $mm^2$; and/or 0.5-20 $mm^2$, such as 1-20 $mm^2$, in order to provide adequate stimulation. For some applications, cathode 54 may be coated with titanium nitride (TiN).

For some applications, each of electrodes 34 has a conduction surface area of at least 2 $mm^2$, such as at least 2.5 $mm^2$, no more than 20 $m^2$, and/or 2-20 $mm^2$, such as 2.5-20 $mm^2$.

For some applications, a conduction surface of each of electrodes 34 is flat or patterned.

For some applications, a conduction surface of each of electrodes 34 comprises microscopic needles, which may increase the contact with the tissue and promote reendothelialization.

For some applications, antenna 28, if provided, is mechanically coupled to frame 30 proximal (e.g., downstream) of prosthetic leaflets 32, such as shown. Alternatively, antenna 28, if provided, is mechanically coupled to frame 30 distal of prosthetic leaflets 32, or at least partially axially overlapping with prosthetic leaflets 32 (configurations not shown).

Reference is still made to FIG. 1. Typically, prosthetic cardiac valve system 10 further comprises an external system that is configured to be disposed outside a body of the patient. The external system comprises an external control unit 50. The external system further comprises an external transmitter and/or receiver, which, for example, may comprise an external coil 52, which is highly schematically illustrated in FIG. 1. For example, external coil 52 may be configured to be placed around the subject's chest, such as schematically shown in FIG. 1, or placed against the chest without surrounding the chest, such as against the sternum (configuration not shown). The external transmitter and/or receiver is configured to drive external coil 52 to wirelessly transfer energy to at least one of the one or more prosthetic-valve coils 36, for example, by inductive coupling. For example, the external transmitter may transmit RF energy at a frequency of 1-300 MHz, e.g., 6.78 MHz.

Figure 2A:
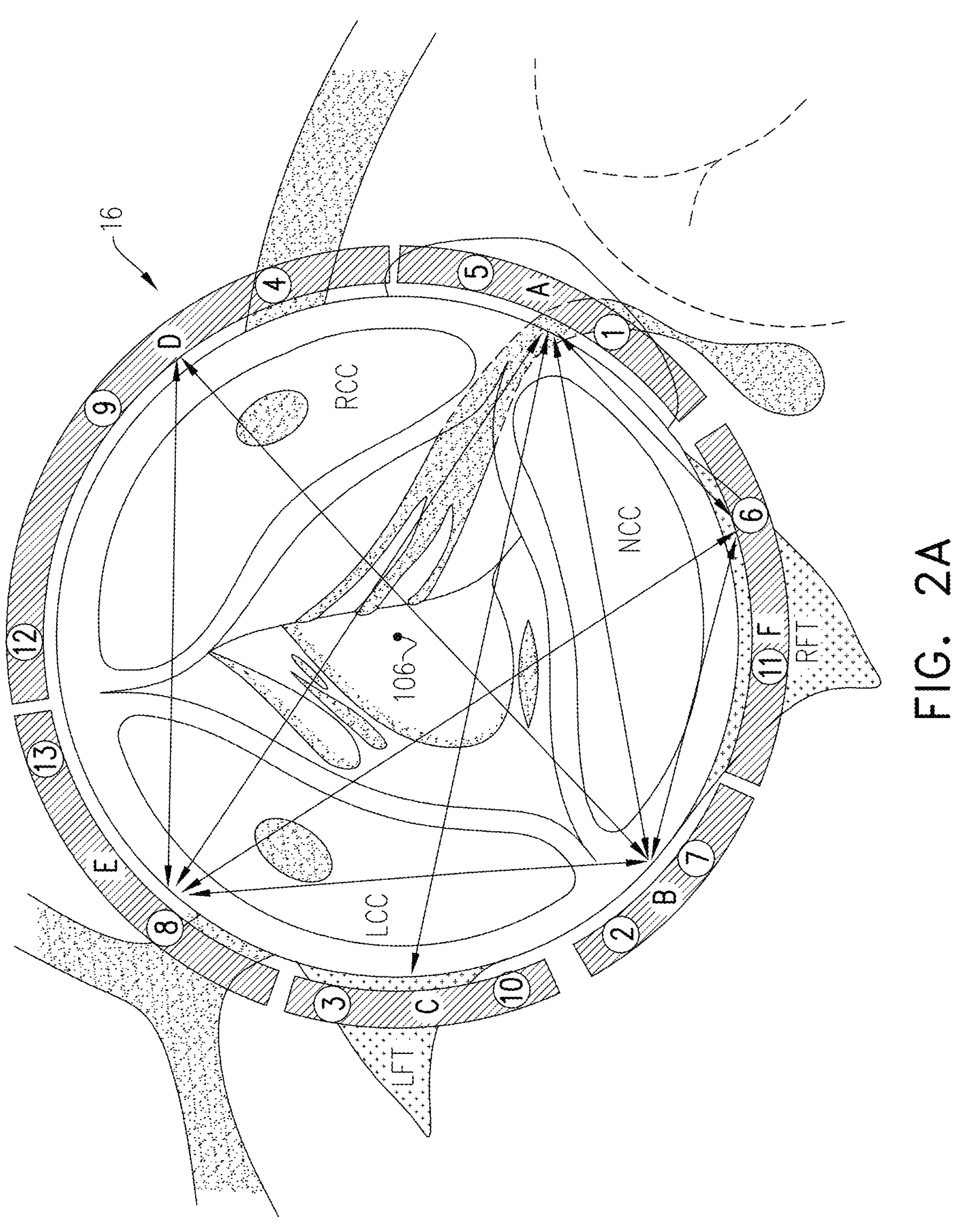
FIGS. 2A-C are schematic cross-sectional illustrations of a native aortic valve from above, indicating angular locations and segments at which pacing pulses may be delivered to the heart, in accordance with respective applications of the present invention.
Figure 2B:
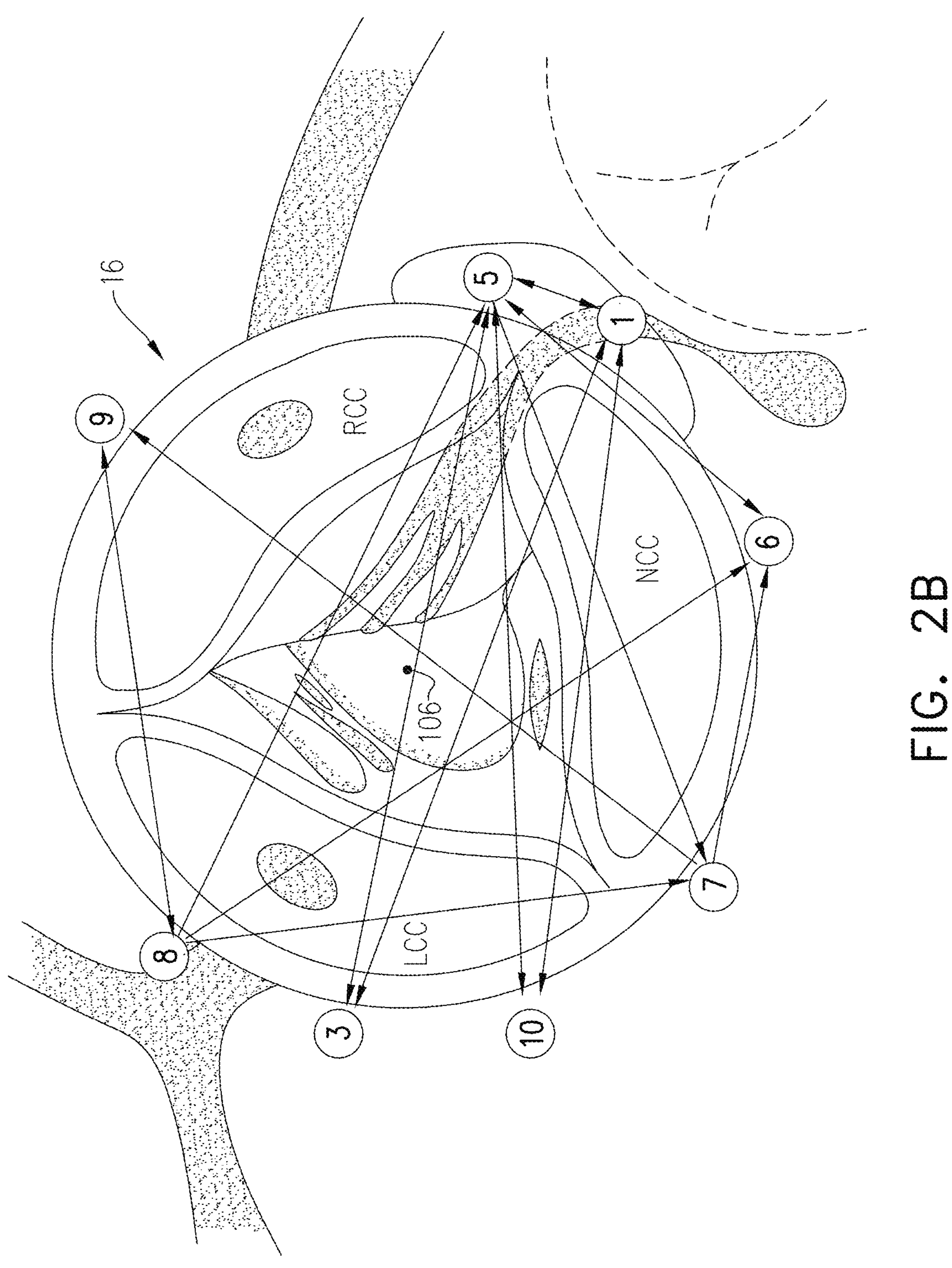
Figure 2C:
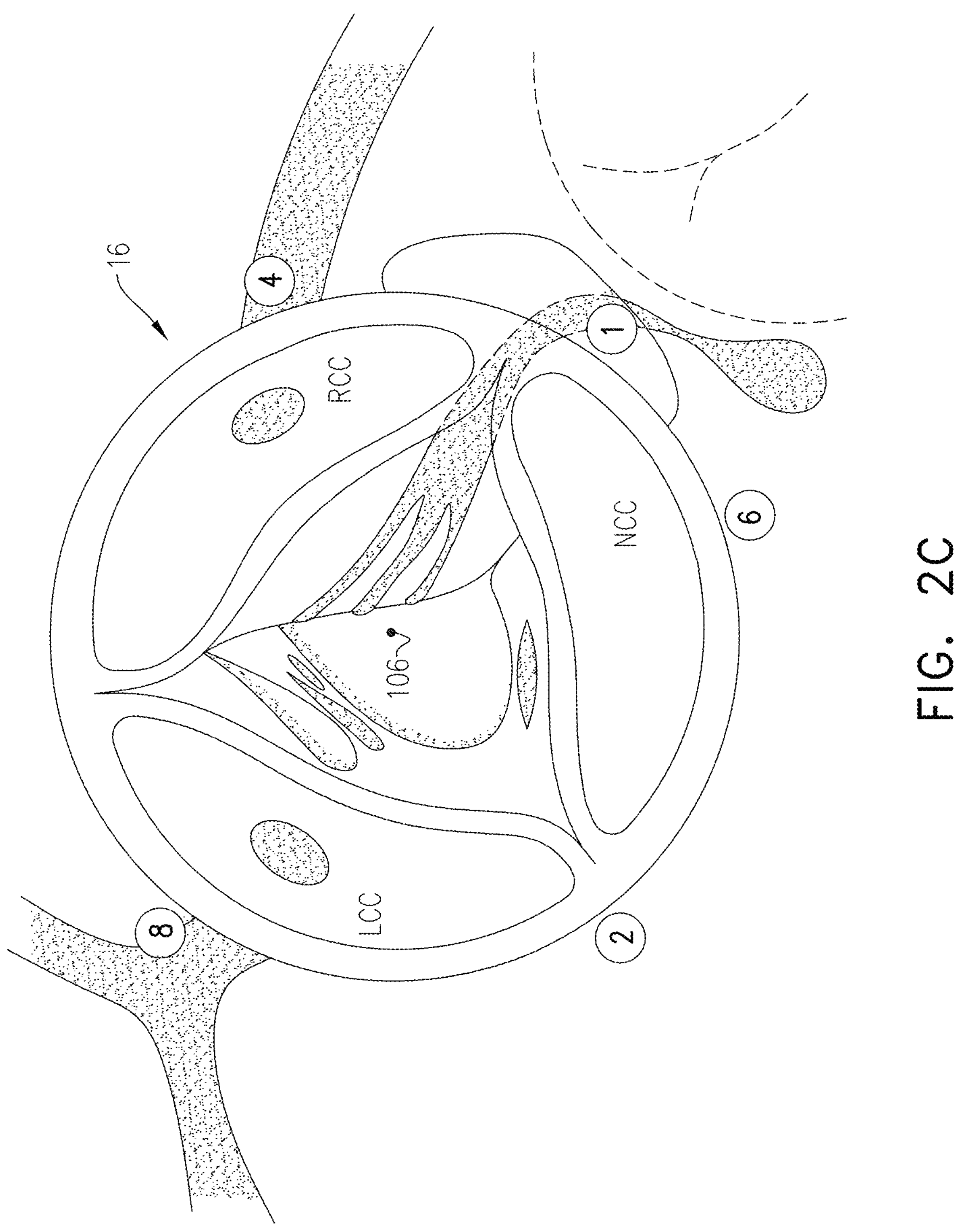

Reference is now made to FIGS. 2A-C, which are schematic cross-sectional illustrations of native aortic valve 16 from above, indicating angular locations and segments at which pacing pulses may be delivered to heart 14, in accordance with respective applications of the present invention. In FIG. 2A, as well as FIGS. 2D and 6B, described hereinbelow, small gaps are shown between the angular segments for clarity of illustration only; in actuality, adjacent angular segments are contiguous with one another, i.e., are not separated by gaps.

Figures 3A, 3B:
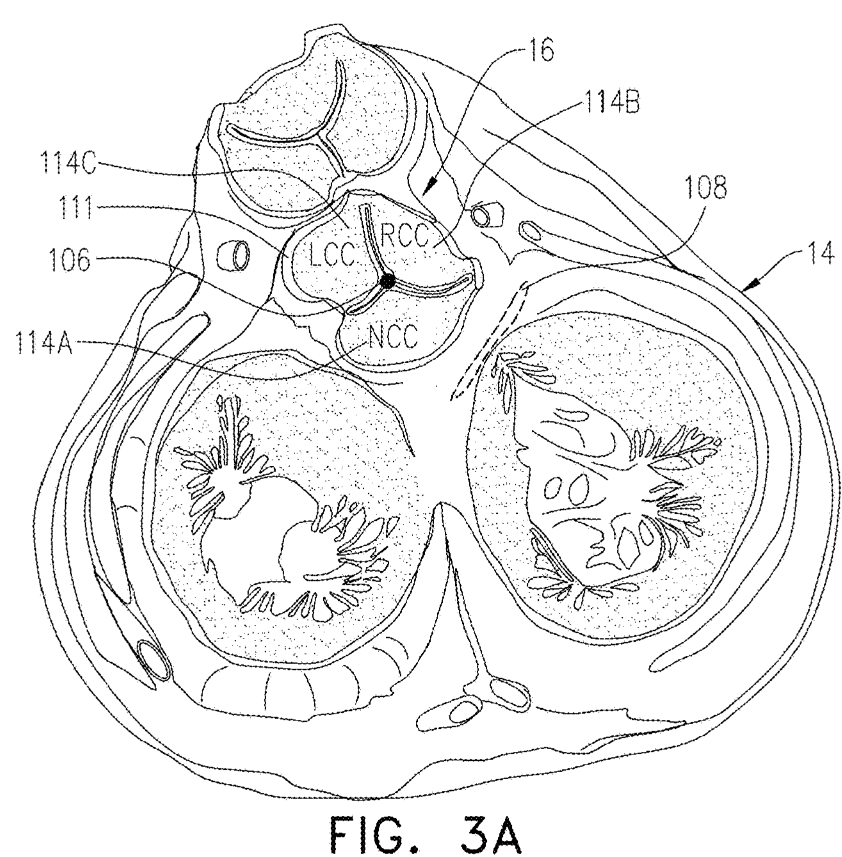
FIGS. 3A and 3B are a schematic cross-sectional view of the heart from above and a schematic side-view in which a portion of the heart and the native aortic valve have been nearly laid open, indicating vertical locations at which pacing pulses may be delivered to the heart, in accordance with respective applications of the present invention.

Reference is also made to FIGS. 3A and 3B, which are a schematic cross-sectional view of heart 14 from above and a schematic side-view in which a portion of heart 14 and native aortic valve 16 have been nearly laid open, indicating vertical locations at which pacing pulses may be delivered to heart 14, in accordance with respective applications of the present invention.

The methods described hereinbelow with reference to FIGS. 2A-C and 3A-B may be performed using prosthetic aortic valve 20, any of the prosthetic aortic valves described in the patents and patent application publications incorporated herein by reference, or other prosthetic aortic valves comprising electrodes, which may be known in the art. Alternatively, these methods may be performed using pacing electrodes inserted into heart 14 and/or the patient's body, or placed in contact with an external surface of the patient's body, as appropriate.

In these methods, each of the pacing pulses are typically delivered with:

- a voltage of at least 0.5 V, no more than 25 V (e.g., no more than 18 V, such as no more than 12 V, e.g., no more than 5 V), and/or 0.5-25 V (e.g., 0.5-18 V, such as 0.5-12 V, e.g., 0.5-5V),
- a current of at least 0.2 milliamps (e.g., at least 0.5 milliamps), no more than 50 milliamps (e.g., no more than 36 milliamps), and/or 0.2-50 milliamps (e.g., 0.5-36 milliamps),
- a pulse duration of at least 0.3 milliseconds, no more than 0.7 milliseconds, and/or 0.3-0.7 milliseconds, and/or
- a pacing frequency of at least 0.5 Hz, no more than 2.5 Hz, and/or 0.5-2.5 Hz.

Typically, the pacing pulses are ventricular pacing pulses. For some applications, the pacing pulses are delivered in VVI mode (Ventricular sensing, Ventricular pacing, Inhibition of pacing when native activity is sensed), DDD mode, VDD mode, or DDDR mode, either with sensing from an implanted electrode or from an external electrode. Alternatively, the pacing pulses may be delivery in another pacing mode, such as any known pacing mode. For other applications, the pacing pulses are delivered in VOO mode (ventricular asynchronous pacing). Optionally, in either the VVI or the VOO mode, rapid pacing is applied.

Angular Locations

Reference is made to FIGS. 2A-B. In some applications of the present invention, pacing pulses are delivered to one or more of the following angular locations, with respect to axis 106 of LVOT 102, set forth in Table 1 and schematically labeled in FIG. 2A and/or FIG. 2B, using techniques described hereinbelow. It is noted that the angular anatomical landmarks may or may not be at the same height as the vertical locations described hereinbelow with reference to FIG. 3B; instead, the angular anatomical landmarks are provided to indicate the angular locations around axis 106 of LVOT 102.

TABLE 1

| Angular Location | Description of Angular Anatomical Landmarks |
|---|---|
| 1 | Adjacent to a membranous septum (MS), below the right lateral end of a non-coronary cusp (NCC) |
| 2 | Adjacent to the aorto-mitral curtain, below an NCC-left coronary cusp (LCC) interleaflet triangle |
| 3 | Adjacent to the anterior end of the left fibrous trigone (LFT) and the left lateral end of the muscular part of the ventricular septum |
| 4 | Adjacent to the muscular part of the ventricular septum, anterior to the membranous septum (MS), across from the right ventricular outflow tract (RVOT), below the middle of a right coronary cusp (RCC) |
| 5 | Adjacent to the membranous septum (MS), below the right lateral end of the RCC |
| 6 | Adjacent to mid-portion of the NCC |
| 7 | Adjacent to the aorto-mitral curtain, below the left-lateral end of the NCC |
| 8 | Adjacent to the left lateral end of the muscular part of the ventricular septum closest to the LFT |
| 9 | Adjacent to the muscular part of the ventricular septum, below the mid-portion of the RCC |
| 10 | Adjacent to the aorto-mitral curtain and the posterior end of the LFT |
| 11 | Adjacent to the mid-portion of the NCC, closer to the NCC-LCC commissure than to the NCC-RCC commissure |
| 12 | Adjacent to the muscular part of the ventricular septum, below the left side of the RCC |
| 13 | Adjacent to the muscular part of the ventricular septum, below the right side of the LCC |

Reference is made to FIG. 2A. In some applications of the present invention, pacing pulses are delivered to one or more of the following angular segments, with respect to axis 106 of LVOT 102, set forth in Table 2 and schematically labeled in FIG. 2A, using techniques described hereinbelow. As also set forth in Table 2, each of the angular segments includes, but is not limited to, one or more of the angular locations set forth in Table 1. It is noted that the angular anatomical landmarks may or may not be at the same height as the vertical locations described hereinbelow with reference to FIG. 3B; instead, the angular anatomical landmarks are provided to indicate the angular locations around axis 106 of LVOT 102.

TABLE 2

| Angular Segment | Description of Angular Anatomical Landmarks | Angular Segment includes Angular Locations |
|---|---|---|
| A | Adjacent to the membranous septum (MS) | 1, 5 |
| B | Adjacent to the aorto-mitral curtain, below the NCC-LCC interleaflet triangle | 2, 7 |
| C | Adjacent to the LFT | 3, 10 |
| D | Adjacent to the anterior-right side of the muscular part of the ventricular septum, below the RCC | 4, 9, 12 |
| E | Adjacent to the muscular part of the ventricular septum, below the anterior side of the LCC | 8, 13 |
| F | Adjacent to the RFT (a/k/a as the Central Fibrous Body) | 6, 11 |

Vertical Locations

Reference is made to FIG. 3B. In some applications of the present invention, pacing pulses are delivered at a vertical location between (a) an upper plane 130 corresponding to an aortic annulus plane 110 and (b) a lower plane 132 parallel to aortic annulus plane 110 and at a distance D below aortic annulus plane 110, distance D equal to 8% of a perimeter of an aortic annulus 111. Alternatively, distance D may be equal to 6% or to 4%. For some applications, the vertical location is between (a) a second distance below upper plane 130, the second distance equal to 2.5% of the perimeter of aortic annulus 111, and (b) lower plane 132.

Horizontal Pacing

Reference is made to FIGS. 2A-B and 3A-B. In an application of the present invention, a method is provided for delivering ventricular pacing pulses to heart 14, the method generally comprising placing first and second electrodes in contact with left ventricular endocardium 100 of a left ventricular outflow tract (LVOT) 102 at a first-electrode site and a second-electrode site, respectively. The ventricular pacing pulses are delivered by driving a pacing signal between the first and the second electrodes, optionally by activating circuitry 40 of prosthetic cardiac valve system 10, described hereinabove with reference to FIG. 1. This pacing protocol is considered "horizontal pacing" because the anode and the cathode are placed at the same distance D below aortic annulus plane 110, or at approximately the same distance D below the aortic annulus plane.

Optionally, in any of the pacing techniques described herein, the pacing signal may be driven between:

- (a) a plurality of first electrodes and (b) the second electrode,
- (a) the first electrode and (b) a plurality of second electrodes, or
- (a) a plurality of first electrodes and (b) a plurality of second electrodes.

For some applications, the method comprises positioning the first electrode in contact with (i.e., in physical contact with) left ventricular endocardium 100 of left ventricular outflow tract (LVOT) 102 at a first-electrode site having:

- a first-electrode angular location with respect to axis 106 of LVOT 102, and
- a first-electrode vertical location between (a) an upper plane 130 corresponding to an aortic annulus plane 110 and (b) a lower plane 132 parallel to aortic annulus plane 110 and at a distance D below aortic annulus plane 110, distance D equal to 8% of a perimeter of an aortic annulus 111; alternatively, distance D may be equal to 6% or to 4%; for some applications, the vertical location is between (a) a second distance below upper plane 130, the second distance equal to 2.5% of the perimeter of aortic annulus 111, and (b) lower plane 132.

For some applications, the method further comprises positioning the second electrode in contact with (i.e., in physical contact with) left ventricular endocardium 100 of left ventricular outflow tract (LVOT) 102 at a second-electrode site having:

- a second-electrode angular location with respect to axis 106 of LVOT 102, the second-electrode angular location different from the first-electrode angular location, and
- a second-electrode vertical location between upper plane 130 and lower plane 132, the second-electrode vertical location the same as or different from the first-electrode vertical location; alternatively, distance D may be equal to 6% or to 4%; for some applications, the vertical location is between (a) a second distance below upper plane 130, the second distance equal to 2.5% of the perimeter of aortic annulus 111, and (b) lower plane 132.

As used in the present application, including in the claims and Inventive Concepts:

- aortic annulus plane 110 is the plane defined by respective nadirs 112A, 112B, and 112C of a non-coronary cusp (NCC) 114A, a right coronary cusp (RCC) 114B, and a left coronary cusp (LCC) 114C (although actually planar, upper and lower planes 130 and 132 are indicated by curved lines in FIG. 2B because the intersections between these planes and left ventricular endocardium 100 of LVOT 102 define respective curves in the nearly laid open view of FIG. 2B);
- aortic annulus 111 is the quasi-circular tissue of LVOT 102 at aortic annulus plane 110;
- an "angular location with respect to axis 106 of LVOT 102" means an angular location around axis 106, i.e., an "o'clock" of the location around the axis, as shown, for example, in FIG. 2A; and
- "vertical" means along a vertical axis that passes vertically from inferior to superior, as defined in human anatomy.

As is known in cardiac anatomy, MS 108 includes both an atrio-ventricular portion and an inter-ventricular portion.

Alternatively, the distance D is 10 mm, 6 mm, or 4 mm.

Reference is still made to FIGS. 2A-B and 3A-B. For some applications, the ventricular pacing pulses are delivered between one of the following pairs of first-electrode angular locations and second-electrode angular locations set forth in Tables 3 and 4, respectively at the first-electrode vertical location and the second-electrode vertical location described above. Either the first electrode is configured as a cathode and the second electrode as an anode, or the first electrode is configured as an anode and the second electrode as a cathode. Each of the pairs of angular locations in Table 3 includes at least one angular segment, and each of the pairs of angular locations in Table 4 includes two angular locations.

TABLE 3

| First-Electrode Angular Location | Second-Electrode Angular Location |
|---|---|
| along Angular Segment A | along Angular Segment B |
| along Angular Segment A | along Angular Segment C |
| along Angular Segment A | at Angular Location 6 |
| along Angular Segment A | at Angular Location 8 |
| along Angular Segment B | along Angular Segment D |
| along Angular Segment B | at Angular Location 6 |
| along Angular Segment B | at Angular Location 8 |
| along Angular Segment D | at Angular Location 8 |
| along Angular Segment E | along Angular Segment D |

TABLE 4

| First-Electrode Angular Location | Second-Electrode Angular Location |
|---|---|
| at Angular Location 1 | at Angular Location 3 |
| at Angular Location 1 | at Angular Location 5 |
| at Angular Location 1 | at Angular Location 10 |
| at Angular Location 3 | at Angular Location 5 |
| at Angular Location 5 | at Angular Location 6 |
| at Angular Location 5 | at Angular Location 7 |
| at Angular Location 5 | at Angular Location 8 |
| at Angular Location 5 | at Angular Location 10 |
| at Angular Location 6 | at Angular Location 7 |
| at Angular Location 6 | at Angular Location 8 |
| at Angular Location 7 | at Angular Location 8 |
| at Angular Location 7 | at Angular Location 9 |
| at Angular Location 8 | at Angular Location 9 |
| at Angular Location 12 | at Angular Location 13 |
| at Angular Location 13 | at Angular Location 9 |

Reference is made to FIGS. 1, 2A-B, and 3A-B. For some applications in which the method is performed using prosthetic aortic valve 20, the first electrode is one of electrodes 34 of prosthetic aortic valve 20, such as first electrode 34A, which is disposed at a distal upstream portion of prosthetic aortic valve 20. The desired first-electrode angular location may be achieved by rotating prosthetic aortic valve 20 during deployment of the valve, and the desired first-electrode vertical location may be achieved by adjusting the vertical (axial) position of prosthetic aortic valve 20 during deployment of the valve.

Reference is still to FIGS. 1, 2A-B, and 3A-B. For some applications, positioning the first electrode comprises:

- delivering a frame, such as frame 30, described hereinabove with reference to FIG. 1, to native aortic valve 16 in a constrained delivery configuration, the frame including interconnected stent struts 90; the first electrode is coupled to the frame; and
- transitioning the frame to an expanded deployment configuration, in which the frame positions and holds the first electrode in contact with left ventricular endocardium 100 of LVOT 102.

For example, the first electrode may be one of electrodes 34 of prosthetic aortic valve 20, such as first electrode 34A, which is disposed at a distal upstream portion of prosthetic aortic valve 20.

For some of these applications, the second electrode is coupled to the frame. The second electrode is positioned in electrical communication with the patient's body by transitioning the frame to the expanded deployment configuration, in which the frame positions and holds the second electrode in contact with left ventricular endocardium 100 of LVOT 102 at the second-electrode angular location and the second-electrode vertical location.

For example, the second electrode may be one of electrodes 34 of prosthetic aortic valve 20, such as another first electrode 34A disposed at a distal upstream portion of prosthetic aortic valve 20 (in which case, electrodes 34 include at least two first electrodes 34A).

For some applications, for delivering ventricular pacing pulses, the first-electrode angular location is selected from the group of angular locations consisting of: (a) an angular location, with respect to axis 106 of LVOT 102, adjacent to a right side of the muscular part of a ventricular septum, below the RCC (Angular Segment D), and (b) an angular location, with respect axis 106 of LVOT 102, adjacent to the muscular part of a ventricular septum, below an anterior side of the LCC (Angular Segment E). In other words, the first-electrode angular extends, with respect to axis 106 of LVOT 102, inclusively, from (a) adjacent to the muscular part of the ventricular septum, anterior to a membranous septum (MS), across from the right ventricular outflow tract (Angular Location 4), (b) around a portion of the RCC, (c) around a portion of the LCC, to (d) adjacent to the left lateral end of the muscular part of a ventricular septum closest to the left fibrous trigone (Angular Location 8).

For some of these application, the first electrode is configured as a cathode and the second electrode as an anode.

For some of these applications, the second-electrode angular location is selected from the group of angular locations consisting of: (a) an angular location, with respect to axis 106 of LVOT 102, adjacent to a right side of the muscular part of a ventricular septum, below the RCC (Angular Segment D), and (b) an angular location, with respect axis 106 of LVOT 102, adjacent to the muscular part of a ventricular septum, below an anterior side of the LCC (Angular Segment E).

Experimental evidence demonstrating successful horizontal ventricular pacing is provided hereinbelow in the descriptions of Experiments #2, #3, and #5.

In some applications of the present invention, a method is provided for delivering atrial pacing pulses to a heart of a patient. The method may optionally implement any of the techniques described herein, including, but not limited to, the techniques described hereinabove in the present section entitled, "Horizontal Pacing." For some applications, the method comprises positioning the first electrode in contact with (i.e., in physical contact with) left ventricular endocardium 100 of left ventricular outflow tract (LVOT) 102 at a first-electrode site having:

- a first-electrode angular location with respect to axis 106 of LVOT 102, and
- a first-electrode vertical location between (a) upper plane 130 corresponding to aortic annulus plane 110 and (b) lower plane 132 parallel to aortic annulus plane 110 and at distance D below aortic annulus plane 110, distance D equal to 8% of a perimeter of an aortic annulus 111; alternatively, distance D may be equal to 6% or to 4%; for some applications, the vertical location is between (a) a second distance below upper plane 130, the second distance equal to 2.5% of the perimeter of aortic annulus 111, and (b) lower plane 132.

For some applications, the method further comprises positioning the second electrode in contact with (i.e., in physical contact with) left ventricular endocardium 100 of left ventricular outflow tract (LVOT) 102 at a second-electrode site having:

- a second-electrode angular location with respect to axis 106 of LVOT 102, the second-electrode angular location different from the first-electrode angular location, and
- a second-electrode vertical location between upper plane 130 and lower plane 132, the second-electrode vertical location the same as or different from the first-electrode vertical location; alternatively, distance D may be equal to 6% or to 4%; for some applications, the vertical location is between (a) a second distance below upper plane 130, the second distance equal to 2.5% of the perimeter of aortic annulus 111, and (b) lower plane 132.

For some applications, for delivering atrial pacing pulses, the first-electrode angular location is along a partially left angular segment 122 (labeled in FIG. 2D) extending, with respect to axis 106 of LVOT 102, inclusively, from (a) adjacent to the anterior end of the LFT and the left lateral end of the muscular part of the ventricular septum (Angular Location 3), (b) around a left posterior portion of LVOT 102, to (c) below a middle of the NCC.

Experimental evidence demonstrating successful horizontal atrial pacing is provided hereinbelow in the descriptions of Experiments #5 and #7.

Vertical Pacing

Reference is made to FIGS. 2C and 3A-B. In an application of the present invention, a method is provided for delivering ventricular pacing pulses to heart 14, the method generally comprising placing a first electrode in contact with left ventricular endocardium 100 of left ventricular outflow tract (LVOT) 102 at a first-electrode site, and a second electrode at a second-electrode site in electrical communication with the patient's body, such as in the aorta (optionally angularly aligned with first-electrode angular location), elsewhere within the patient's body (such as in contact with the heart, e.g., pericardium of the heart), or on an external surface of skin of the patient's body, e.g., using a patch electrode). The ventricular pacing pulses are delivered by driving a pacing signal between the first and the second electrodes, optionally by activating circuitry 40 of prosthetic cardiac valve system 10, described hereinabove with reference to FIG. 1. This pacing protocol is considered "vertical pacing" because one of the electrodes is placed above aortic annulus plane 110 and the other electrode is placed below aortic annulus plane 110.

For some applications, the method comprises positioning the first electrode in contact with (i.e., in physical contact with) left ventricular endocardium 100 of left ventricular outflow tract (LVOT) 102 at a first-electrode site having:

- a first-electrode angular location with respect to axis 106 of LVOT 102, and
- a first-electrode vertical location between (a) upper plane 130 corresponding to aortic annulus plane 110 and (b) lower plane 132 parallel to aortic annulus plane 110 and at distance D below aortic annulus plane 110, distance D equal to 8% of a perimeter of an aortic annulus 111; alternatively, distance D may be equal to 6% or to 4%; for some applications, the vertical location is between (a) a second distance below upper plane 130, the second distance equal to 2.5% of the perimeter of aortic annulus 111, and (b) lower plane 132.

Reference is still made to FIGS. 2C and 3A-B. For some applications, the ventricular pacing pulses are delivered between (a) one of the following first-electrode angular locations set forth in Tables 5 and 6 and (b) the second-electrode site in the aorta, optionally angularly aligned with first-electrode angular location. Either the first electrode is configured as a cathode and the second electrode as an anode, or the first electrode is configured as an anode and the second electrode as a cathode. Each of the locations in Table 5 includes one angular segment, and each of the angular locations in Table 6 includes one angular location.

TABLE 5

| First-Electrode Angular Location |
|---|
| along Angular Segment A |
| along Angular Segment B |
| along Angular Segment D |

TABLE 6

| First-Electrode Angular Location |
|---|
| at Angular Location 1 |
| at Angular Location 2 |
| at Angular Location 4 |
| at Angular Location 6 |
| at Angular Location 8 |

Reference is made to FIGS. 1, 2C, and 3A-B. For some applications in which the method is performed using prosthetic aortic valve 20, the first electrode is one of electrodes 34 of prosthetic aortic valve 20, such as first electrode 34A, which is disposed at a distal upstream portion of prosthetic aortic valve 20. The desired first-electrode angular location may be achieved by rotating prosthetic aortic valve 20 during deployment of the valve, and the desired first-electrode vertical location may be achieved by adjusting the vertical (axial) position of prosthetic aortic valve 20 during deployment of the valve.

Interleaflet Triangles

Reference is made to FIG. 3B. In some applications of the present invention, the first-electrode site is on an interleaflet triangle 134 of native aortic valve 16. Optionally, the first-electrode site is closer to aortic annulus plane 110 than to a plane defined by respective commissures of the three cusps of native aortic valve 16 (i.e., the first-electrode site is in a lower half of one of the interleaflet triangles 134).

The second-electrode site is in electrical communication with within a body of the patient, such as in the aorta (optionally angularly aligned with first-electrode angular location), elsewhere within the patient's body (such as in contact with the heart, e.g., pericardium of the heart), or on an external surface of skin of the patient's body, e.g., using a patch electrode). The ventricular pacing pulses a delivered by driving a pacing signal between the first and the second electrodes.

For some applications, the second-electrode site is in the aorta, for performing "vertical pacing," such as described hereinabove, mutatis mutandis. Optionally, the second electrode is positioned at the second-electrode site in the aorta angularly aligned with first-electrode site.

For some applications, the interleaflet triangle is a first interleaflet triangle, and the second-electrode site is on a second interleaflet triangle of the aortic valve.

For other applications, the second-electrode site is at a (a) at one of the Angular Locations set forth in Table 1 hereinabove and/or along one of the Angular Segments set forth in Table 2 hereinabove, and (b) a vertical location between upper plane 130 and lower plane 132, as described hereinabove with reference to FIG. 3B.

Experimental evidence demonstrating successful inter-leaflet triangle pacing is provided hereinbelow in the description of Experiment #4.

Horizontal Sensing

Figure 2D:
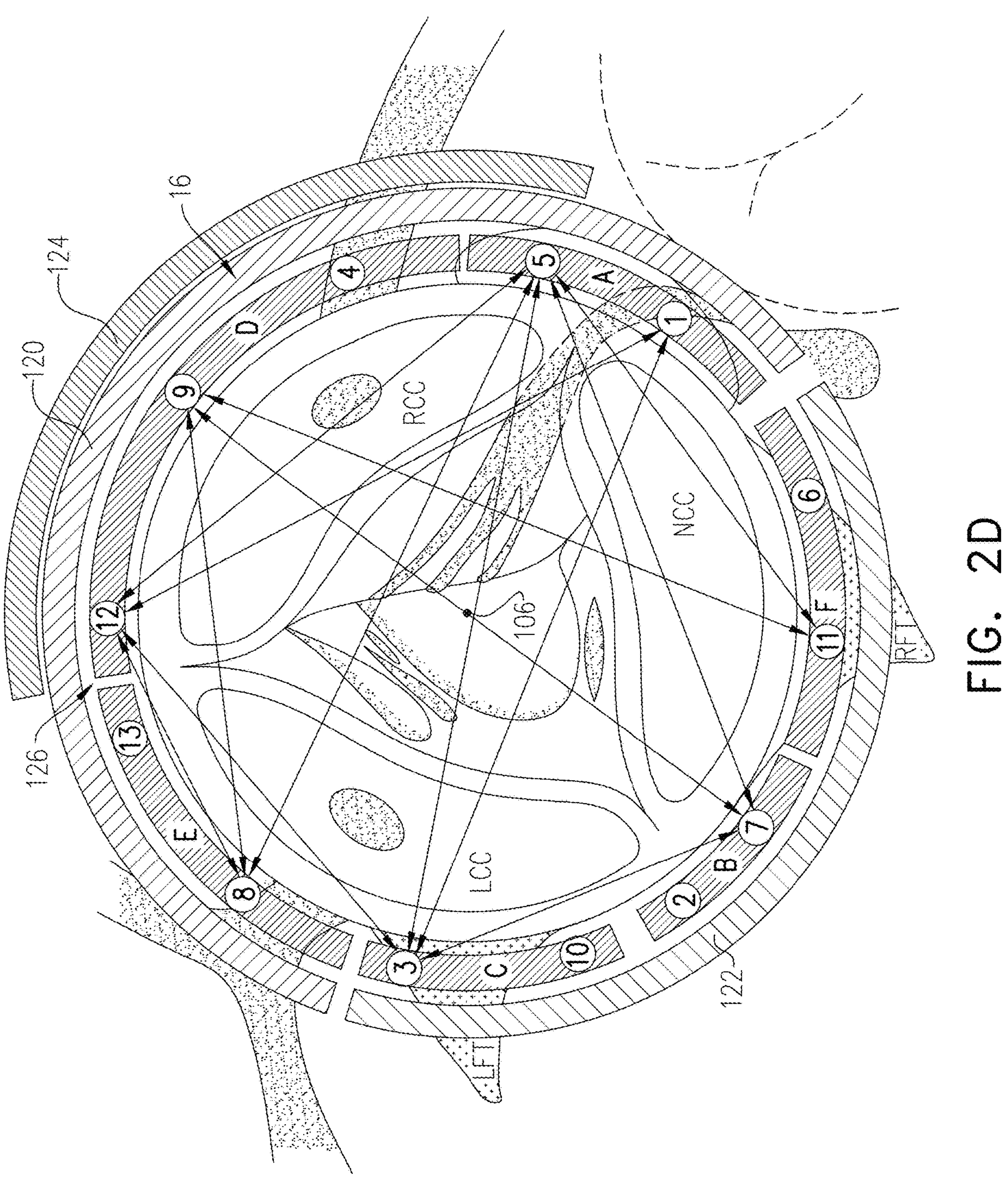
FIG. 2D is a schematic cross-sectional illustration of the native aortic valve from above, indicating angular locations and segments at which electrical activity of the heart may be sensed, in accordance with respective applications of the present invention.

Reference is now made to FIG. 2D, which is a schematic cross-sectional illustration of native aortic valve 16 from above, indicating angular locations and segments at which electrical activity of heart 14 may be sensed, in accordance with respective applications of the present invention. Reference is also again made to FIGS. 3A-B.

In some applications of the present invention, a method is provided for sensing electrical activity of heart 14, the method generally comprising placing first and second electrodes in contact with left ventricular endocardium 100 of a left ventricular outflow tract (LVOT) 102 at a first-electrode site and a second-electrode site, respectively. The electrical activity of heart 14 is sensed between the first and the second electrodes (i.e., bipolar sensing), optionally by activating circuitry 40 of prosthetic cardiac valve system 10, described hereinabove with reference to FIG. 1. Typically, circuitry 40 is activated to attempt to identify a ventricular activation signal and/or an atrial activation signal in an intracardiac electrogram (EGM) sensed using the first and the second electrodes. This sensing protocol is considered "horizontal sensing" because the anode and the cathode are placed at the same distance D below aortic annulus plane 110, or at approximately the same distance D below the aortic annulus plane.

For some applications, circuitry 40 is configured to attempt to identify the intrinsic ventricular activation signal and/or the atrial activation signal in the intracardiac EGM by sensing using only the first and the second electrodes.

For some applications, circuitry 40 is configured to identify the intrinsic ventricular activation signal and/or the atrial activation signal in the intracardiac EGM by configuring the first and the second electrodes as a cathode and as an anode, respectively. Alternatively, for some applications, circuitry 40 is configured to identify the intrinsic ventricular activation signal and/or the atrial activation signal in the intracardiac EGM by configuring the first and the second electrodes as an anode and as a cathode, respectively.

These sensing techniques may implement any of the techniques described herein for pacing, mutatis mutandis, including techniques for positioning the electrodes.

Experimental evidence demonstrating successful horizontal sensing is provided hereinbelow in the descriptions of Experiments #6 and #7. In general, the experimental evidence demonstrates that the polarity of the two electrodes (which is the cathode and which is the anode) does not have a substantial effect on the signal quality (reversing the polarity of the electrodes simply reverses the signal polarity).

Optionally, in any of the sensing techniques described herein, the electrical activity may be sensed between:

(a) a plurality of first electrodes and (b) the second electrode, (a) the first electrode and (b) a plurality of second electrodes, or (a) a plurality of first electrodes and (b) a plurality of second electrodes.

For some applications, the method comprises positioning the first electrode in contact with (i.e., in physical contact with) left ventricular endocardium 100 of left ventricular outflow tract (LVOT) 102 at a first-electrode site having:

a first-electrode angular location with respect to axis 106 of LVOT 102, and a first-electrode vertical location between (a) an upper plane 130 corresponding to an aortic annulus plane 110 and (b) a lower plane 132 parallel to aortic annulus plane 110 and at a distance D below aortic annulus plane 110, distance D equal to 8% of a perimeter of an aortic annulus 111; alternatively, distance D may be equal to 6% or to 4%; for some applications, the vertical location is between (a) a second distance below upper plane 130, the second distance equal to 2.5% of the perimeter of aortic annulus 111, and (b) lower plane 132.

For some applications, the method further comprises positioning the first electrode in contact with (i.e., in physical contact with) left ventricular endocardium 100 of left ventricular outflow tract (LVOT) 102 at a second-electrode site having:

a second-electrode angular location with respect to axis 106 of LVOT 102, the second-electrode angular location different from the first-electrode angular location, and a second-electrode vertical location between upper plane 130 and lower plane 132, the second-electrode vertical location the same as or different from the first-electrode vertical location; alternatively, distance D may be equal to 6% or to 4%; for some applications, the vertical location is between (a) a second distance below upper plane 130, the second distance equal to 2.5% of the perimeter of aortic annulus 111, and (b) lower plane 132.

In some applications of the present invention:

the first-electrode site has (i) the first-electrode vertical location described immediately above, and (ii) a first-electrode angular location, with respect to axis 106 of LVOT 102, along a partially anterior angular segment 120 extending, with respect to axis 106 of LVOT 102, inclusively, from (a) the posterior end of a membranous septum (MS), (b) around an anterior portion of LVOT 102, to (c) the anterior end of the LFT, and the second-electrode site has (i) the second-electrode vertical location described immediately above, and (ii) a second-electrode angular location, with respect to axis 106 of LVOT 102, along partially anterior angular segment 120, the second-electrode angular location different from the first-electrode angular location.

For some of these applications, circuitry 40 is activated to sense an intrinsic (i.e., non-pacing-induced) ventricular activation signal and/or atrial activation signal in the intracardiac EGM. For others of these applications, circuitry 40 is activated to sense a pacing-induced ventricular activation signal and/or atrial activation signal in the intracardiac EGM.

For some applications, the first-electrode angular location is along a sub-segment of the partially anterior angular segment 120, the sub-segment extending, with respect to axis 106 of LVOT 102, inclusively, from (a) adjacent to the membranous septum (MS), below a right lateral end of the NCC (Angular Location 1), (b) around the anterior portion of LVOT 102, to (c) the anterior end of the LFT.

For some applications, the first-electrode angular location is along a sub-segment of partially anterior angular segment 120, the sub-segment extending, with respect to axis 106 of LVOT 102, inclusively, from (a) the posterior end of membranous septum (MS), (b) around the anterior portion of LVOT 102, to (c) adjacent to the left lateral end of the muscular part of the ventricular septum closest to a left fibrous trigone (LFT) (Angular Location 8). For some of these applications, the first-electrode angular location is along a sub-segment of the partially anterior angular segment, the sub-segment extending, with respect to axis 106 of LVOT 102, inclusively, from (a) adjacent to the membranous septum (MS), below a right lateral end of the NCC, (b) around the anterior portion of the LVOT, to (c) adjacent to the left lateral end of the muscular part of the ventricular septum closest to a left fibrous trigone (LFT) (Angular Location 8).

For some applications, the second-electrode angular location is offset from the first-electrode angular location by at least 10 degrees, such as at least 20 degrees, with respect to axis 106 of LVOT 102.

For some applications, the first-electrode angular location is adjacent to the left lateral end of the muscular part of a ventricular septum closest to a left fibrous trigone (Angular Location 8). For some of these applications, the second-electrode angular location is:

- adjacent to the muscular part of a ventricular septum, below a left side of the RCC (Angular Location 12),
- adjacent to the muscular part of a ventricular septum, below the mid-portion of the RCC (Angular Location 9), or
- adjacent to a membranous septum (MS), below a right lateral end of the NCC (Angular Location 5).

For some applications, the first-electrode angular location is adjacent to the muscular part of a ventricular septum, below a left side of the RCC (Angular Location 12). For some of these applications, the second-electrode angular location is:

- adjacent to a membranous septum (MS), below a right lateral end of the NCC (Angular Location 5), or
- adjacent to a membranous septum (MS), below a right lateral end of the RCC (Angular Location 1).

For some applications, the first-electrode angular location is adjacent to the muscular part of a ventricular septum, below the mid-portion of the RCC (Angular Location 9).

For some applications, the first-electrode angular location is adjacent to a membranous septum (MS), below a right lateral end of the NCC (Angular Location 5).

For some applications, the first-electrode angular location is adjacent to a membranous septum (MS), below a right lateral end of the RCC (Angular Location 1).

In some applications of the present invention:

- the first-electrode site has (i) the first-electrode vertical location described above, and (ii) a first-electrode angular location, with respect to axis 106 of LVOT 102, along partially left angular segment 122 extending, with respect to axis 106 of LVOT 102, inclusively, from (a) adjacent to the anterior end of the left fibrous trigone (LFT) and the left lateral end of the muscular part of a ventricular septum (Angular Location 3), (b) around a left posterior portion of LVOT 102, to (c) below a middle of the NCC; and
- the second-electrode site has (i) the second-electrode vertical location described above, and (ii) a second-electrode angular location, with respect to axis 106 of LVOT 102, along partially left angular segment 122, the second-electrode angular location different from the first-electrode angular location.

For some applications, the second-electrode angular location is offset from the first-electrode angular location by at least 10 degrees, such as at least 20 degrees, e.g., at least 30 degrees, with respect to axis 106 of LVOT 102.

For some applications, the first-electrode angular location is adjacent to an anterior end of the left fibrous trigone and a left lateral end of the muscular part of a ventricular septum (Angular Location 3). For some of these applications, the second-electrode angular location is adjacent to an aorto-mitral curtain and a posterior end of the left fibrous trigone (Angular Location 7).

For some applications, the first-electrode angular location is adjacent to an aorto-mitral curtain and a posterior end of the left fibrous trigone (Angular Location 7). For some of these applications, the second-electrode angular location is below the middle of the NCC (Angular Location 11).

For some applications, the first-electrode angular location is below the middle of the NCC (Angular Location 11).

In some applications of the present invention:

- the first-electrode site has (i) the first-electrode vertical location described above, and (ii) a first-electrode angular location, with respect to axis 106 of LVOT 102, along a partially anterior angular segment 124 extending, with respect to axis 106 of LVOT 102, inclusively, from (a) adjacent to a membranous septum (MS), below the right lateral end of the RCC, (b) around an anterior portion of LVOT 102, to (c) adjacent to an RCC-LCC commissure 126; and
- the second-electrode site has (i) the second-electrode vertical location described above, and (ii) a second-electrode angular location, with respect to axis 106 of LVOT 102, along a partially left angular segment extending, with respect to axis 106 of LVOT 102, inclusively, from (a) adjacent to an anterior end of a left fibrous trigone (LFT) and a left lateral end of the muscular part of a ventricular septum, (b) around a left posterior portion of LVOT 102, to (c) below a middle of the NCC.

For some applications, such as for sensing a ventricular activation signal, the first-electrode angular location is (a) adjacent to a right side of the muscular part of a ventricular septum, below a right coronary cusp (RCC) (Angular Segment D), (b) adjacent to the muscular part of a ventricular septum, below an anterior side of a left coronary cusp (LCC) (Angular Segment E), or (c) adjacent to a membranous septum (Angular Segment A).

For some applications, such as for sensing an atrial activation signal, the first-electrode angular location is along a segment that extends, with respect to an axis of the LVOT, inclusively, from (a) adjacent to an anterior end of a left fibrous trigone (LFT) and a left lateral end of the muscular part of a ventricular septum (Angular Location 3), (b) around a posterior portion of the LVOT, to (c) adjacent to a membranous septum (MS), below a right lateral end of a right coronary cusp (RCC) (Angular Location 5).

Generally-Applicable Techniques

Reference is made to FIGS. 1, 2A-D, and 3A-B. For some applications, positioning the first electrode comprises:

- delivering a frame, such as frame 30, described hereinabove with reference to FIG. 1, to native aortic valve 16 in a constrained delivery configuration, the frame including interconnected stent struts 90; the first electrode is coupled to the frame; and transitioning the frame to an expanded deployment configuration, in which the frame positions and holds the first electrode in contact with left ventricular endocardium 100 of LVOT 102.

For example, the first electrode may be one of electrodes 34 of prosthetic aortic valve 20, such as first electrode 34A, which is disposed at a distal upstream portion of prosthetic aortic valve 20.

For some of these applications, the second electrode is coupled to the frame. The second electrode is positioned in electrical communication with the patient's body by transitioning the frame to the expanded deployment configuration, in which the frame positions and holds the second electrode at a second-electrode vertical location above (i.e., superior to) aortic annulus plane 110 in contact with blood and not in contact with an aortic wall. For example, the second electrode may be one of electrodes 34 of prosthetic aortic valve 20, such as second electrode 34B, which is disposed at a proximal downstream portion of prosthetic aortic valve 20.

For some applications, positioning first electrode 34A at the first-electrode site and positioning second electrode 34B at the second-electrode site comprise:

- delivering a support to an aortic position in the heart in a constrained delivery configuration; first and second electrodes 34A and 34B are coupled to the support; and
- transitioning the support to an expanded deployment configuration, in which the support positions and holds first and second electrodes 34A and 34B in contact with left ventricular endocardium 100 of the LVOT 102 at the first-electrode and the second-electrode sites, respectively.

For some of these applications, the method further comprising introducing a prosthetic aortic valve into a body of the patient and placing the prosthetic aortic valve within the support, the prosthetic aortic valve including a plurality of prosthetic leaflets arranged so as to allow blood flow in a downstream direction and inhibit blood flow in an upstream direction.

For other applications, positioning the second electrode in electrical communication with the patient's body comprises positioning the second electrode elsewhere in the patient's body (such as in contact with the heart, e.g., with pericardium of the heart), or on an external surface of skin of the patient's body, e.g., using a patch electrode (configuration not shown).

Reference is still made to FIGS. 1, 2A-D, and 3A-B. For some applications, delivering the ventricular pacing pulses comprises configuring the first electrode as an anode and the second electrode a cathode. For other applications, delivering the ventricular pacing pulses comprises configuring the first electrode as a cathode and the second electrode an anode.

Experimental evidence demonstrating successful vertical pacing is provided hereinbelow in the descriptions of Experiments #1 and #2.

Experimental Evidence

Reference is now made to FIGS. 4 and 5A-D, which are schematic illustrations showing results of seven experiments conducted by the inventors, using techniques similar to some of those described herein. Any of the techniques described in these experiments may optionally be incorporated into the techniques of the inventions described herein, as appropriate.

Experiment #1

A first experiment conducted by the inventors was designed to assess the minimal pacing voltage for ventricular cardiac pacing using electrodes disposed at various electrode locations on an external surface of a frame of a prosthetic aortic valve similar to prosthetic aortic valve 20 described hereinabove with reference to FIG. 1. This experiment was designed to assess "vertical pacing," as described hereinabove with reference to FIGS. 1, 2C, and 3A-B. The prosthetic aortic valve had a diameter of 27 mm, and was implanted transapically in the native aortic valves of two pigs having weights of 92 kg and 94 kg. (A pig model is widely recognized for its close similarity to humans.)

Figure 4:
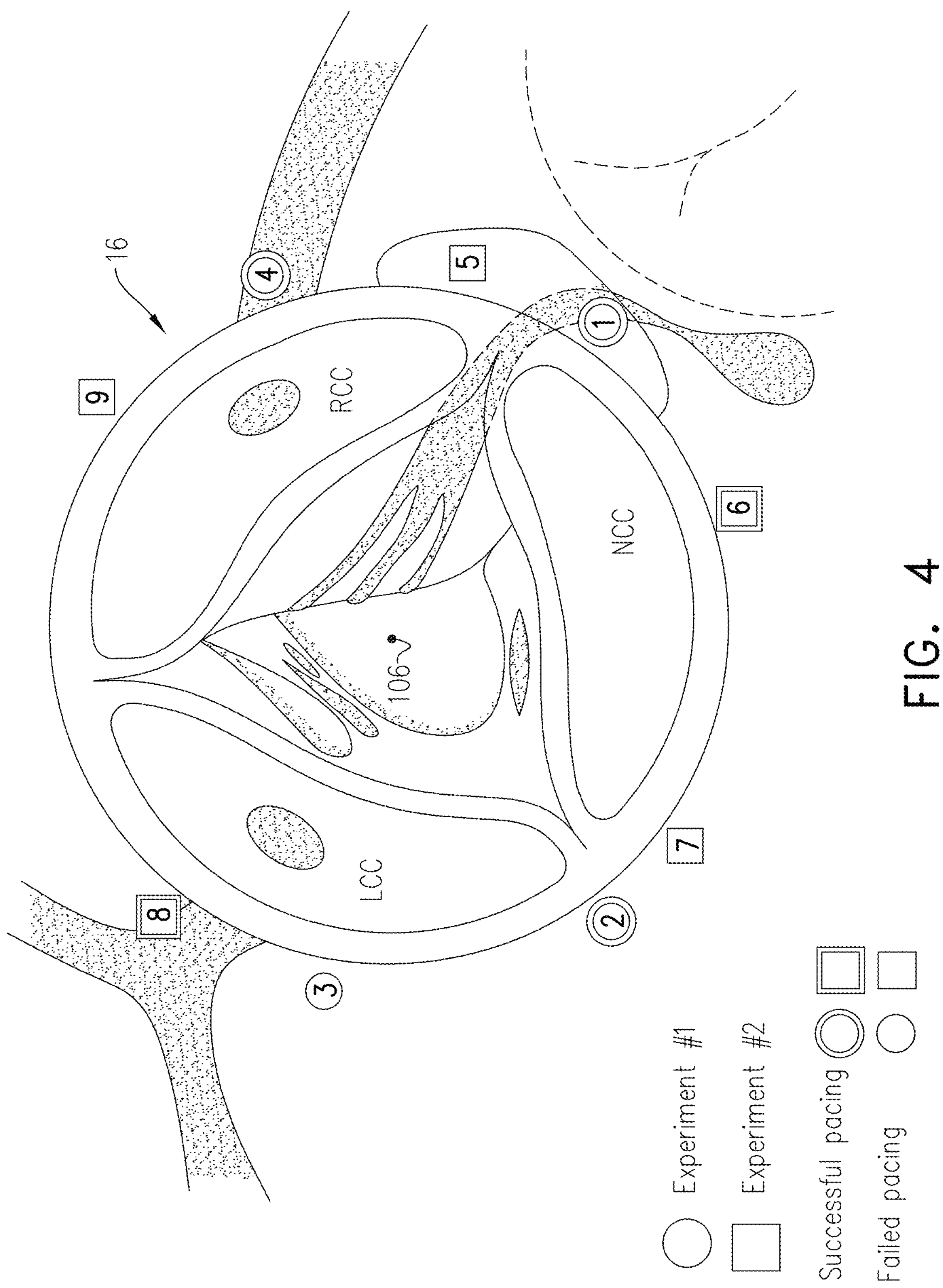
FIGS. 4 and 5A-D are schematic illustrations showing results of seven experiments conducted by the inventors, using techniques similar to those described herein.

The results of Experiment #1 are summarized schematically in FIG. 4, in which the pacing angular locations of this experiment are schematically indicated by circled numbers 1, 2, 3, and 4, using the numbers for the angular locations set forth hereinabove in Table 1.

Pacing was attempted, each time through a different pair of electrodes, and the minimal voltage for ventricular pacing (as registered through an external ECG device) was recorded. Two different pulse generators were used: Osypka 101 PG (Osypka Medical, Berlin, Germany) (output given in volts); and the Medtronic 5392 PG (Medtronic, Minneapolis, Minnesota) (output given in mA). The electrodes were directly, non-wirelessly connected to the pulse generators. Power was calculated as the product of the outputted volts and outputted mA. The pulse generators were configured to pace higher than the intrinsic cardiac rate of the animals, in an asynchronous mode. Pairs of matching leads were connected to the two pulse generators. For each pair of leads, the minimal pacing voltage at which the set pace dominated the animal's cardiac rate (as registered in the ECG) was measured.

Each pair of electrodes included an anode and a cathode. One of two electrodes was disposed super-annularly on the frame of the prosthetic aortic valve, angularly aligned with the other of the two electrodes. The other of the two electrodes was disposed sub-annularly, approximately 4-8 mm below the annulus, at Angular Locations 1, 2, 3, and 4 set forth in Table 1 hereinabove.

The following Table 7 summarizes the results at each of the cathode Angular Locations, using the numbers set forth in Table 1 hereinabove:

TABLE 7

| Cathode Angular Location | Min. voltage for pacing [V] | Min. current for pacing [mA] | Min. power for pacing [mW] |
|---|---|---|---|
| 4 | Unknown (>12) | 7-8 | Unknown, estimated ~112 |
| 1 | 3 | 1.5 | 4.5 |
| 3 | — | — | — |
| 2 | 8 | 3.5 | 28 |

As can be seen in Table 7, successful ventricular pacing was achieved at Angular Locations 1, 2, and 3. The level of contact between the electrode ends and the tissue was not measured. Insufficient contact between the exposed electrode and the tissue may explain the high variability in power threshold between the angular locations; however, no evidence for this was identified.

Experiment #2

A second experiment conducted by the inventors was designed to assess the minimal pacing voltage for ventricular cardiac pacing using electrodes disposed at various electrode locations on an external surface of a frame of a prosthetic aortic valve similar to prosthetic aortic valve 20 described hereinabove with reference to FIG. 1. This experiment was designed to assess both "vertical pacing" and "horizontal pacing," as described hereinabove with reference to FIGS. 1, 2A-B, and 3A-B. Other than as described below, the second experiment was conducted in a similar manner to Experiment #1 described hereinabove. The electrodes comprised exposed wire leads, which were directly, non-wirelessly connected to the pulse generators. The prosthetic aortic valve had a diameter of 27 mm, and was implanted transapically in the native aortic valves of two pigs having weights of about 90 kg.

The results of Experiment #2 are summarized schematically partially in FIG. 4 and partially in FIG. 5A, in which the pacing locations of this experiment are schematically indicated by numbers 5, 6, 7, 8, and 9 in squares, using the numbers set forth in Table 1 hereinabove.

In a first set of electrode placements similar to those described in Experiment #1, "vertical pacing" was performed. Each pair of electrodes included an anode and a cathode. The anode was disposed super-annularly on the frame of the prosthetic aortic valve, angularly aligned with the cathode. The cathode was disposed sub-annularly, approximately 3-5 mm below the annulus, at Angular Locations 5, 6, 7, 8, and 9 set forth in Table 1 hereinabove.

The following Table 8 summarizes the results at each of the cathode Angular Locations, using the numbers set forth in Table 1 hereinabove:

TABLE 8

| Cathode Angular Location | Min. voltage for pacing [V] | Min. current for pacing [mA] | Min. power for pacing [mW] |
|---|---|---|---|
| 9 | No pacing (>18 V) | | |
| 6 | 13 | 28.9* | 375.6* |
| 5 | No pacing (>18 V) | | |
| 8 | 6 | 13.3* | 80* |
| 7 | No pacing (>18 V) | | |

*Values estimated based on impedance derived from nearby measurements

As can be seen in Table 8, successful pacing was achieved at Angular Locations 6 and 8.

In a second set of electrode placements, "horizontal pacing" was performed. Each pair of electrodes included an anode and a cathode, both of which were disposed sub-annularly, approximately 3-5 mm below the annulus, at two different angular locations. Each pair of electrodes is schematically labeled in FIG. 5A by a connecting line, the ends of which indicate the angular locations of the anode and the cathode. As indicated in the key in FIG. 5A, the endpoints of the lines indicate which electrode was an anode (by a circle) and which electrode was a cathode (by a square), or that both sets of polarities were tested (by both circles and squares at both endpoints of the lines). (The lines connect the electrode pairs only schematically, and may or may not indicate the actual conduction paths between the electrode pairs, which were not measured in the experiment.)

The following Table 9 summarizes the results for each of the pairs of Angular Locations, using the numbers set forth in Table 1 hereinabove:

TABLE 9

| Anode Angular Location | Cathode Angular Location | Min. voltage for pacing [V] |
|---|---|---|
| 9 | 8 | 9.5 |
| 7 | 9 | 17 |
| 6 | 5 | 5.6 |
| 5 | 7 | 7 |
| 8 | 5 | 6 |
| 8 | 6 | 12 |
| 7 | 6 | 12 |
| 8 | 7 | 10 |
| 5 | 6 | 5.6 |

As can be seen, successful pacing was achieved at all pairs of Angular Locations. The best pacing, as indicated by the minimum voltage required to achieve pacing, was achieved at the following pairs of Angular Locations (Anode-Cathode respectively): 5-6, 6-5, 8-5, and 5-7.

Observed values for pacing [V] and impedance [ohms] were overall consistent through repeated measurement. However, a minor decline in performance over consecutive measurements was observed: the second and third pacing attempts, where performed, required slightly stronger stimulation output to achieve pacing.

Experiment #3

A third experiment conducted by the inventors was designed to assess the minimal pacing voltage for ventricular cardiac pacing using electrodes disposed at various electrode locations on an external surface of a frame of a prosthetic aortic valve similar to prosthetic aortic valve 20 described hereinabove with reference to FIG. 1. Other than as described below, the third experiment was conducted in a similar manner to the horizontal pacing portion of Experiment #2 described hereinabove. The prosthetic aortic valve had a diameter of 27 mm, and was implanted transapically in the native aortic valve of one pig having a weight of 104 kg.

The results of Experiment #3 are summarized schematically in FIG. 5A, in which the pacing locations of this experiment are schematically indicated by numbers 1, 3, 5, and 10 in pentagons, using the numbers set forth in Table 1 hereinabove.

Each pair of electrodes included an anode and a cathode, both of which were disposed sub-annularly, approximately 4-6 mm below the annulus, at two different angular locations. Unlike in Experiments #1 and #2, in Experiment #3 an external transmitter was used to wirelessly transmit energy to the implant, which delivered the energy as DC current stimulation to the tissue through the selected electrodes. The system enabled, by wireless commands from the external transmitter, configuration of each electrode to be a cathode or an anode.

Figure 5A:
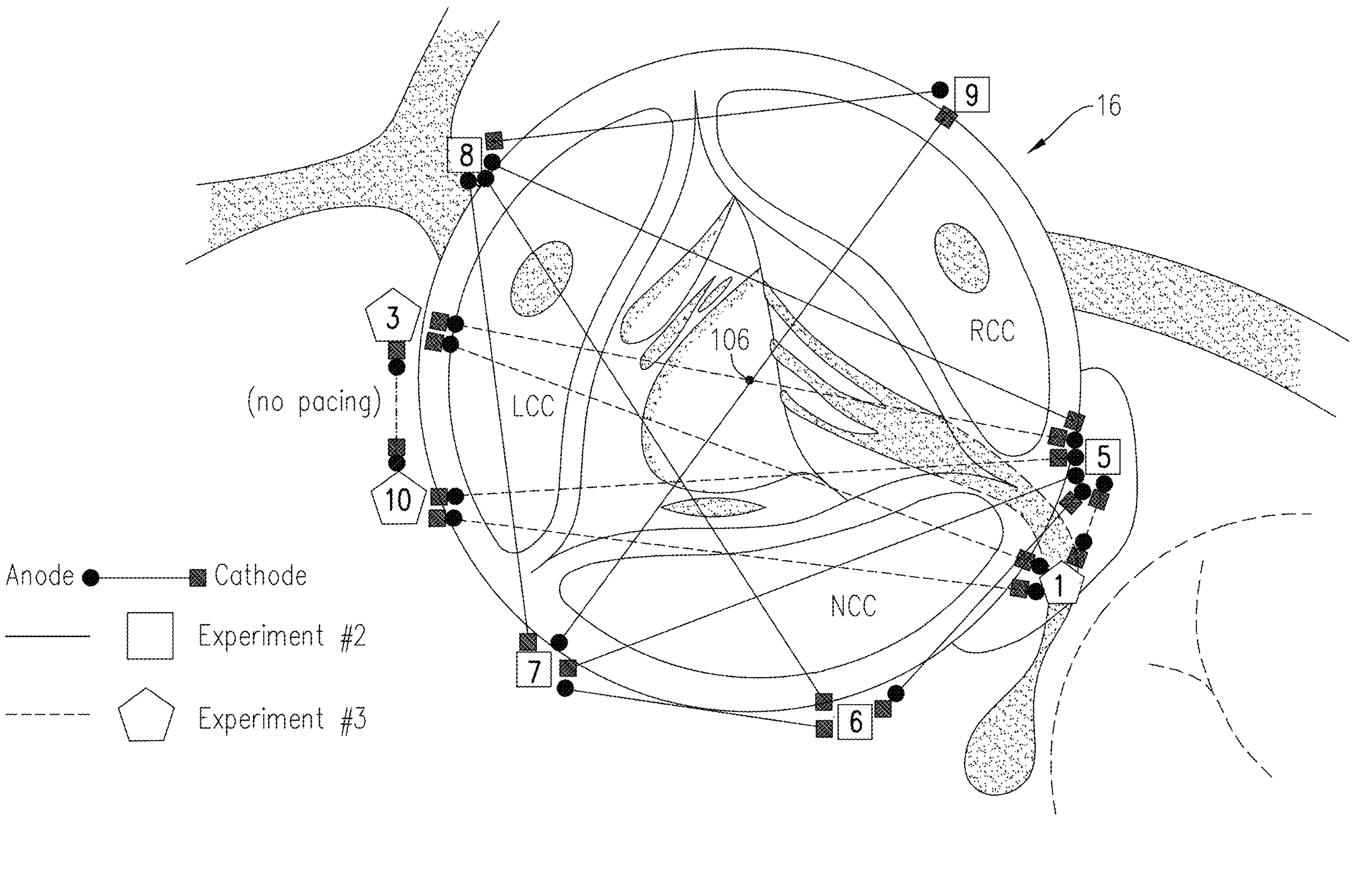

Each pair of electrodes is schematically labeled in FIG. 5A by a connecting line, the ends of which indicate the angular locations of the anode and the cathode. As indicated in the key in FIG. 5A, the endpoints of the lines indicate which electrode was an anode (by a circle) and which electrode was a cathode (by a square), or that both sets of polarities were tested (by both circles and squares at both endpoints of the lines). (The lines connect the electrode pairs only schematically, and may or may not indicate the actual conduction paths between the electrode pairs, which were not measured in the experiment.)

The following Table 10 summarizes the results for each of the pairs of Angular Locations, using the numbers set forth in Table 1 hereinabove; as mentioned above, each pair was tested twice, in both directions of stimulation, and is thus listed twice in the table. The pacing currents presented in Table 10 represent the current that flowed through the induction coil of the transmitter in the external transmitter, rather than the current applied to the cardiac tissue by the electrodes; thus, the values cannot be directly compared to the values presented in Tables 7, 8, and 9 for Experiments #1 and #2.

TABLE 10

| Anode Angular Location | Cathode Angular Location | Min. current for pacing [A] |
|---|---|---|
| 10 | 5 | 1.8 |
| 5 | 1 | 4.2 |
| 5 | 10 | 5 |
| 1 | 5 | 1.8 |
| 3 | 5 | 1.8 |
| 5 | 3 | 1.8 |
| 1 | 10 | 5.4 |
| 10 | 1 | 4.2 |
| 1 | 3 | 5.3 |
| 3 | 1 | 4 |
| 3 | 10 | No Pacing |
| 10 | 3 | No Pacing |

As can be seen, successful ventricular pacing was achieved at all pairs of Angular Locations except the pair of Angular Locations 3 and 10, with both polarities. The best ventricular pacing, as indicated by the minimum voltage required to achieve ventricular pacing, was achieved at the following pairs of Angular Locations (Anode-Cathode, respectively): 10-5, 1-5, 3-5, and 5-3.

As can be seen, the best ventricular pacing, as indicated by the minimum voltage required to achieve ventricular pacing, was achieved using arcs that included Angular Location 5 and/or Angular Location 1, both positioned near the bundle of His, with Angular Location 5 providing lower pacing thresholds. Better pacing with any given pair of electrodes was achieved when the cathode was placed at Angular Location 5 or Angular Location 1 than when the anode was placed at this location.

No degradation of performance was observed after pacing from a certain point multiple times.

Experiment #4

A fourth experiment conducted by the inventors was designed to assess whether cardiac ventricular pacing could be achieved using cathodes disposed at various electrode locations on and above the LVOT. This experiment was designed to assess feasibility of pacing by stimulation at various points in and around the heart, as described hereinabove with reference to FIG. 3B. Cathode leads and anode leads were assembled on semi-rigid rods and placed at the locations set forth in Table 11 below in a pig having a weight of 90 kg. Intracardiac and intra-aortic locations were reached via a transapical sheath. Pacing was attempted, each time at a different electrode location, and whether pacing was achieved was recorded. A Medtronic 5348 temporary pulse generator was used (Medtronic, Minneapolis, Minnesota).

Table 11 presents ventricular pacing results of Experiment #4:

TABLE 11

| Anode Location | Cathode Location | Pacing achieved? |
|---|---|---|
| Within the trans-apical sheath | Within the trans-apical sheath | No |
| In LVOT against atrio-ventricular wall | On the pericardium | Yes |
| In LV, no contact with endocardium | LV, no contact with endocardium | No |
| In the LV on the endocardium | In the LV space, no tissue contact | No |
| Against aortic root wall | In the lv space, no tissue contact | No |
| In the Aortic root without tissue contact | In the LV against the endocardium | No |
| Touching the aortic root wall | Between the NCC-RCC commissure and aortic annulus plane 110 | Yes |
| Touching the aortic root wall | Between the NCC-LCC commissure and aortic annulus plane 110 | Yes |
| Touching the aortic root wall | Between the RCC-LCC commissure and aortic annulus plane 110 | No |
| At annulus on anterior side of valve | Between the NCC-RCC commissure and annulus plane 110 | Yes |
| Touching the aortic root wall | Touching the aortic root wall | No |

* Position of the electrode was estimated based on the imaging capabilities at hand but could not be precisely verified.

As can be seen, successful ventricular pacing was achieved when the cathode was in contact with the interleaflet triangle between the NCC-RCC commissure and aortic annulus plane 110, and with the interleaflet triangle between the NCC-LCC commissure and aortic annulus plane 110, but not with the interleaflet triangle between the RCC-LCC commissure and aortic annulus plane 110.

Successful ventricular pacing was also achieved when the cathode was in contact with the interleaflet triangle between the NCC-RCC commissure and aortic annulus plane 110 and the anode was at the annulus level against the anterior side of the aortic valve.

Experiment #5

A fifth experiment conducted by the inventors was designed, among other things, to assess the minimal pacing voltage required to achieve ventricular or atrial pacing using electrodes disposed at various electrode locations on an external surface of a frame of a prosthetic aortic valve similar to prosthetic aortic valve 20 described hereinabove with reference to FIG. 1. Other than as described below, the fifth experiment was conducted in a similar manner to the horizontal pacing portion of Experiment #2 described hereinabove, and in a similar manner to Experiment #3 described hereinabove. The prosthetic aortic valve had a diameter of 27 mm and included eight electrodes disposed at various respective angular locations with respect to a central longitudinal axis of the frame. The prosthetic aortic valve was implanted transapically in the native aortic valve of four pigs having a weight of 100±5 kg.

Figure 5B:
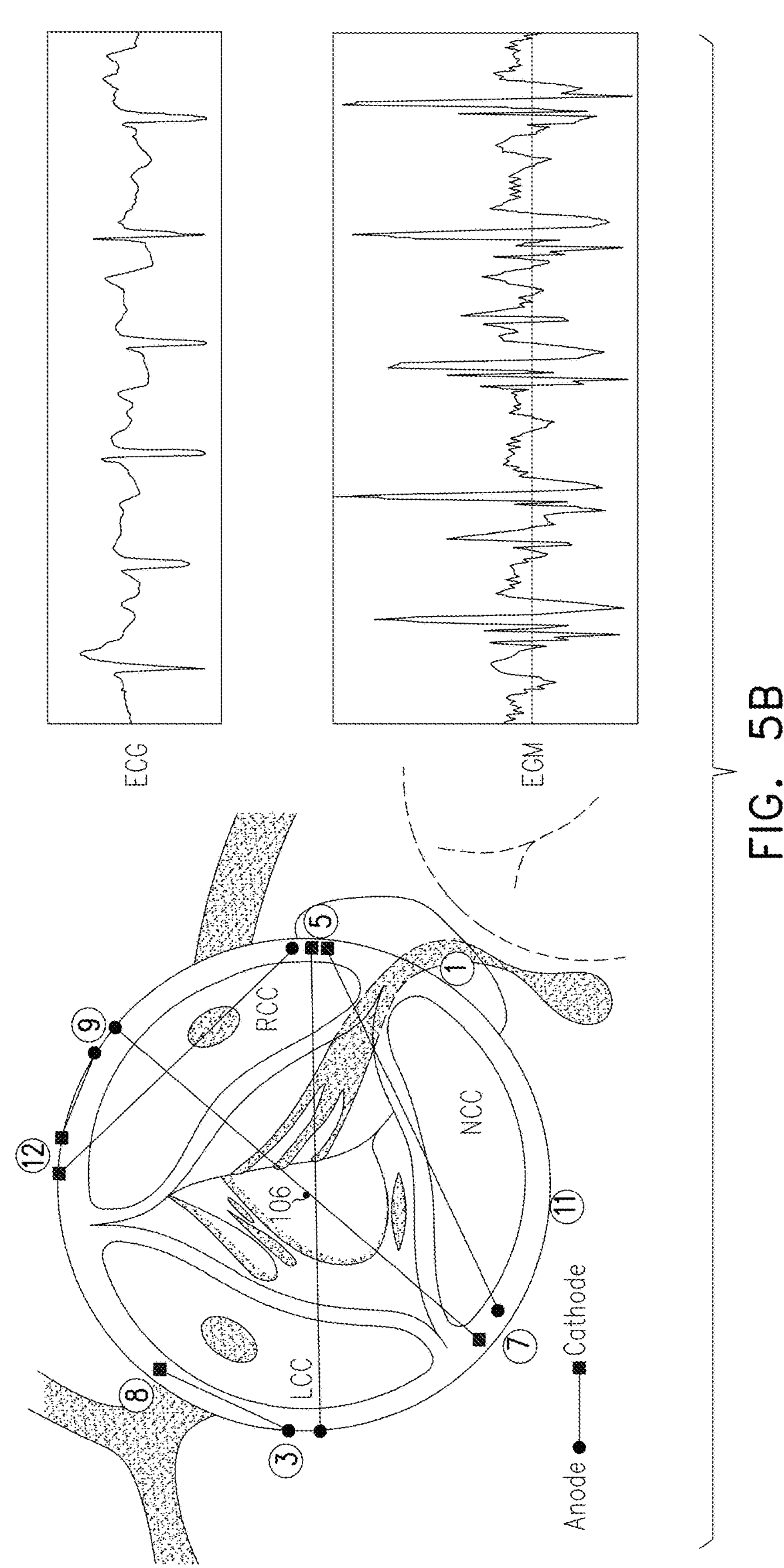
Figure 5C:
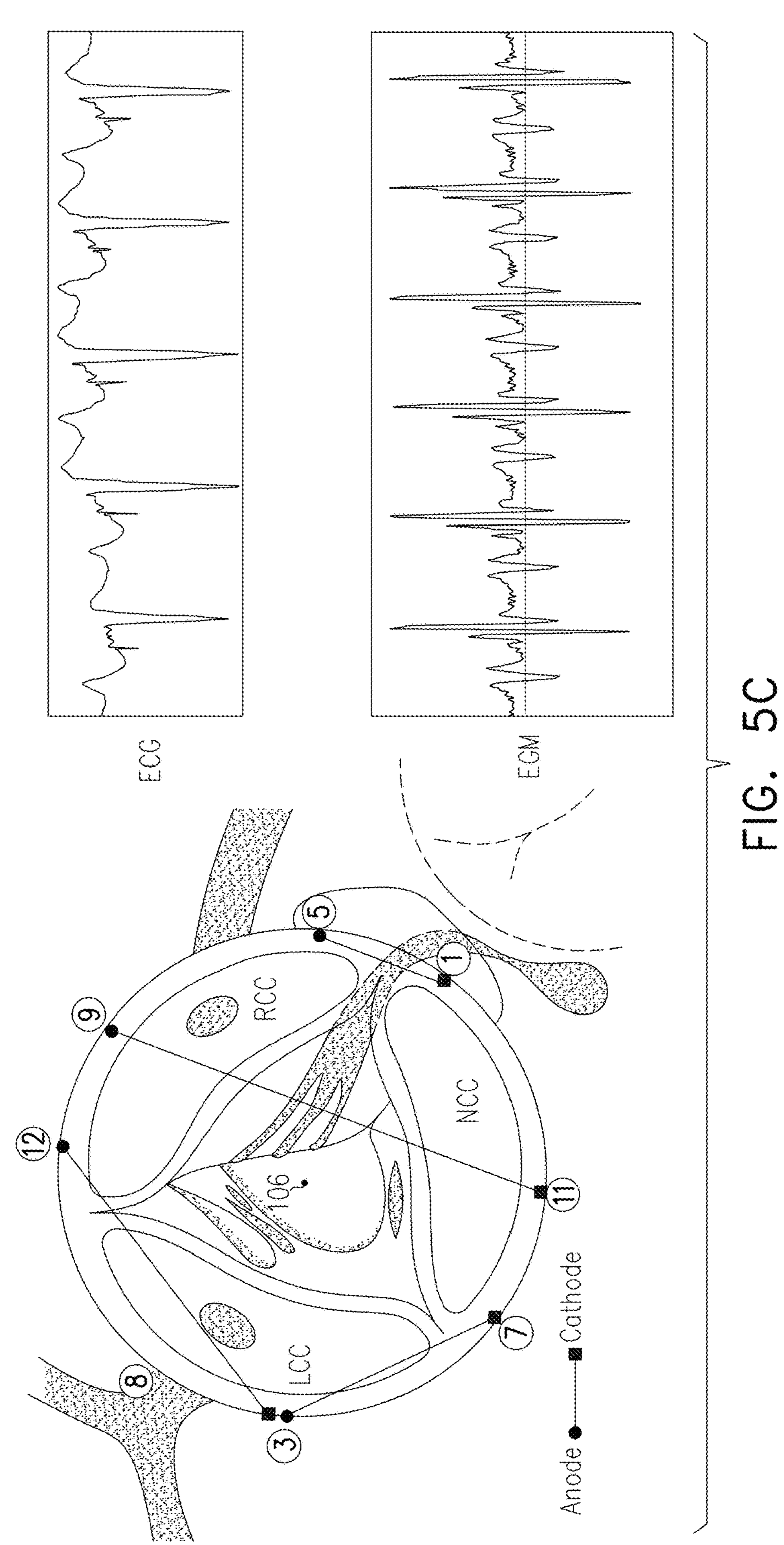

The results of a first portion of Experiment #5 are summarized schematically in FIGS. 5B and 5C, in which the pacing locations of this experiment are schematically indicated by circled numbers 1, 3, 5, 7, 8, 9, 11, and 12, using the numbers for the angular locations set forth hereinabove in Table 1. FIG. 5B shows pacing locations that achieved ventricular pacing with zero activation time (stimulus-to-QRS interval), and FIG. 5C shows pacing locations that achieved ventricular pacing with delayed activation). The pairs that successfully achieved ventricular pacing are labeled in FIG. 5B or FIG. 5C, and the pairs that achieved atrial pacing are labeled in FIG. 5D.

FIGS. 5B and 5C also show one set of representative ECG and EGM traces (ECG and EGM traces were produced for the other pacing locations as well). The ECG traces were acquired conventionally, using external ECG skin electrodes on the chest. The EGM trace shown in FIG. 5B was acquired using a pair of electrodes at Anode Angular Location 11 and Cathode Angular Location 7 during pacing between Anode Angular Location 5 and Cathode Angular Location 12. The EGM trace shown in FIG. 5C was acquired using a pair of electrodes at Anode Angular Location 1 and Cathode Angular Location 5 during pacing between Anode Angular Location 12 and Cathode Angular Location 3.

Each pair of electrodes included an anode and a cathode, both of which were disposed sub-annularly, approximately 4-6 mm below the annulus, at two different angular locations. As in Experiments #1, #2, and #4, the electrodes were directly, non-wirelessly connected to the pulse generator. The system enabled, by wireless commands from the external transmitter, configuration of each electrode to be a cathode or an anode.

Each pair of electrodes is schematically labeled in FIGS. 5B-C by a connecting line, the ends of which indicate the angular locations of the anode and the cathode. As indicated in the key in FIGS. 5B-C, the endpoints of the lines indicate which electrode was an anode (by a circle) and which electrode was a cathode (by a square). (The lines connect the electrode pairs only schematically, and may or may not indicate the actual conduction paths between the electrode pairs, which were not measured in the experiment.)

The following Table 12 summarizes the results for each of the pairs of Angular Locations, using the numbers set forth in Table 1 hereinabove. Only the pairs that successfully achieved ventricular pacing are labeled in FIG. 5B or FIG. 5C, while the pairs that successfully achieved atrial pacing are labeled in FIG. 5D, described hereinbelow.

TABLE 12

| Anode Angular Location | Cathode Angular Location | Min. Voltage For Pacing [V] | Type of Pacing Induced* |
|---|---|---|---|
| 9 | 11 | 7** | II |
| 9 | 12 | 7** | I |
| 5 | 9 | 8** | II |
| 5 | 1 | 6 | II |
| 5 | 12 | 6 | I |
| 7 | 11 | 10 | A |
| 3 | 8 | 8.5 | I |
| 3 | 7 | 3.6 | II |
| 3 | 12 | 5.6 | II |
| 1 | 7 | 4 | A |
| 9 | 7 | 3.6 | I |
| 8 | 7 | 3.8 | II |
| 8 | 1 | 1.4 | II |
| 3 | 5 | 1.4 | I |
| 7 | 5 | 1.4 | I |

*I = zero activation time; II = delayed activation; A = atrial pacing.

**Unlike the other voltages set forth in Table 12, the voltages labeled with an asterisk do not represent the minimum voltage capable of causing pacing, but instead a single voltage that was tested and resulted in pacing.

Figure 6A:
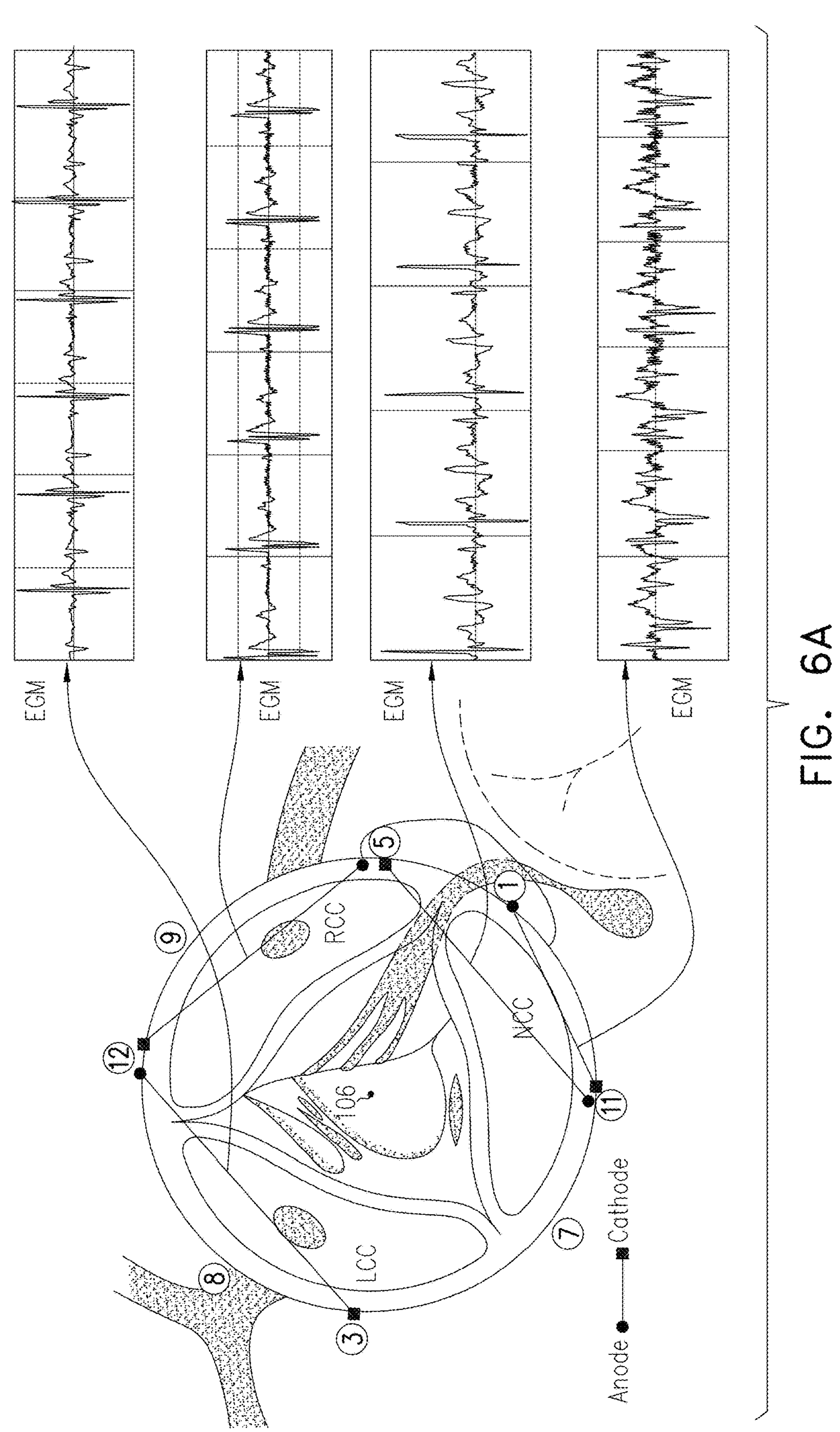
FIGS. 6A-B are schematic illustrations showing results of another experiment conducted by the inventors, using techniques similar to some of those described herein.
Figure 6B:
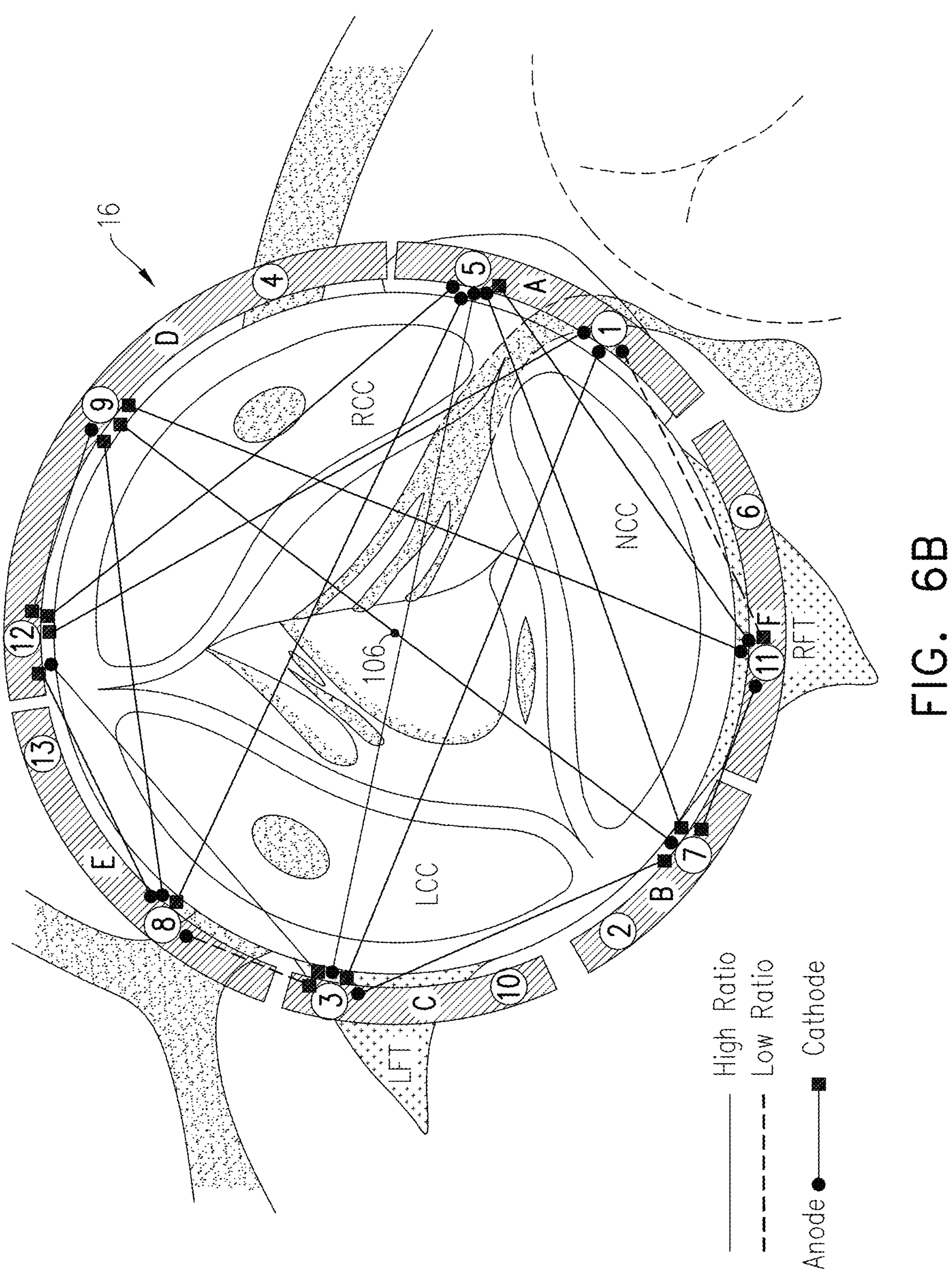

Reference is now made to FIGS. 6A-B, which are schematic illustrations showing results of an additional experiment conducted by the inventors, using techniques similar to some of those described herein. Any of the techniques described in this experiment may optionally be incorporated into the techniques of the inventions described herein, as appropriate.

Experiment #6

A sixth experiment conducted by the inventors was designed to assess the feasibility of accurate sensing of a ventricular activation signal in an EGM sensed using two of the electrodes disposed at various electrode locations on an external surface of a frame of a prosthetic aortic valve similar to prosthetic aortic valve 20 described hereinabove with reference to FIG. 1. Experiment #6 was performed together with Experiment #5, described hereinabove, using the same experimental procedure.

A portion of the results of Experiment #6 are summarized schematically in FIGS. 6A-B, in which the sensing locations of this experiment are schematically indicated by circled numbers, using the numbers for the angular locations set forth hereinabove in Table 1. Table 13 below lists all of the pairs shown in FIGS. 6A-B.

Each pair of electrodes included an anode and a cathode, both of which were disposed sub-annularly, approximately 4-6 mm below the annulus, at two different angular locations.

Each pair of electrodes is schematically labeled in FIGS. 6A-B by a connecting line, the ends of which indicate the angular locations of the anode and the cathode. As indicated in the key in FIGS. 6A-B, the endpoints of the lines indicate which electrode was an anode (by a circle) and which electrode was a cathode (by a square). (The lines connect the electrode pairs only schematically, and may or may not indicate the actual conduction paths between the electrode pairs, which were not measured in the experiment.)

Sensing was attempted of the heart's natural electrical activity, without pacing, each time through a different pair of electrodes.

For each pair of electrodes, an EGM was measured and the voltage of the highest amplitude component (as an average of all the spikes) of the signal was identified as representing the ventricular activation signal. The second-highest amplitude component (generally as an average of all the spikes) of the signal was also identified, and the ratio between the voltage of the highest amplitude component and the voltage of the second-highest amplitude component was calculated. If the highest amplitude component had a positive voltage, the next-highest amplitude component with a positive voltage was identified; if the highest amplitude component had a negative voltage, the next-highest amplitude component with a negative voltage was identified.

The following Table 13 summarizes the results for each of the pairs of Angular Locations, using the numbers set forth in Table 1 hereinabove, including a V-Signal Separation Ratio (VSR), which is the ratio between the ventricular component and the second-highest component of the signal:

TABLE 13

| Anode angular location | Cathode angular location | Ventricular activation signal [mV] | Second-highest component [mV] | VSR |
|---|---|---|---|---|
| 11 | 5 | 1.2 | 0.31 | 3.9 |
| 11 | 9 | −1.13 | −0.21 | 5.4 |
| 1 | 12 | −1.6 | −0.19 | 8.7 |
| 11 | 7 | 0.98 | 0.22 | 3.3 |
| 3 | 7 | 1.66 | 0.25 | 6.6 |
| 8 | 12 | 1.6 | 0.41 | 4.0 |
| 8 | 9 | 1.66* | 0.54 | 3.1 |
| 8 | 3 | 0.43 | 0.28 | 1.5 |
| 12 | 3 | 1.67* | 0.29 | 5.8 |
| 1 | 3 | −1.67* | −0.28 | 6.0 |
| 5 | 12 | −1.66* | −0.27 | 6.1 |

TABLE 13-continued

| Anode angular location | Cathode angular location | Ventricular activation signal [mV] | Second-highest component [mV] | VSR |
|---|---|---|---|---|
| 5 | 7 | 1.19 | 0.48 | 2.7 |
| 1 | 11 | −0.54 | −0.43 | 1.3 |
| 5 | 8 | −1.66* | −0.3 | 5.5 |
| 7 | 9 | 1.66* | 0.44 | 3.8 |
| 9 | 7 | 1.66* | 0.47 | 3.5 |
| 5 | 3 | −1.66* | −0.14 | 11.9 |

*Technological constraints in this experiment limited the measured EGM voltage to between −1.66 or −1.67 and +1.66 mV. Actual values may be higher.

As can be seen in Table 13, in all of the tested pairs the ventricular signal was distinct and significantly higher than the second-highest component of the signal, except for one acquisition through electrodes at Anode Angular Location 1 and Cathode Angular Location 11, and for one acquisition through electrodes at Anode Angular Location 8 and Cathode Angular Location 3, in which the ventricular signal was only modestly higher than the second-highest component of the signal.

Experiment #7

A seventh experiment conducted by the inventors was designed, among other things, to assess the minimal pacing voltage required to achieve atrial pacing using electrodes disposed at various electrode locations on an external surface of a frame of a prosthetic aortic valve similar to prosthetic aortic valve 20 described hereinabove with reference to FIG. 1. Other than as described below, the seventh experiment was conducted in a similar manner to the horizontal pacing portion of Experiment #2 described hereinabove, and in a similar manner to Experiment #3 described hereinabove, except that the electrodes in Experiment #7 comprised gold-plated copper pads. The prosthetic aortic valve had a diameter of 27 mm and included eight electrodes disposed at various respective angular locations with respect to a central longitudinal axis of the frame. The prosthetic aortic valve was implanted transapically in the native aortic valve of one pig having a weight of 100 kg.

Figure 5D:
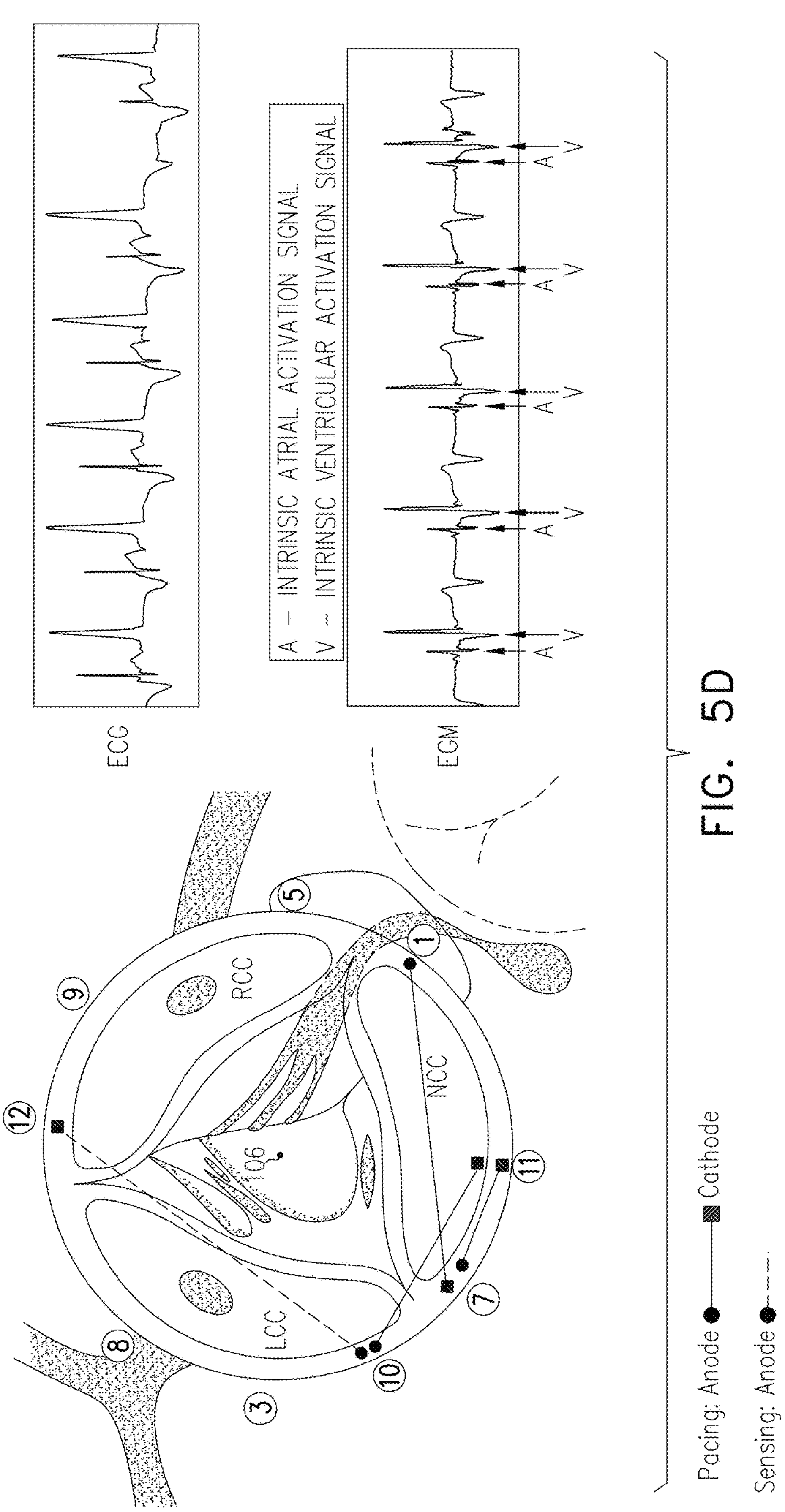

The results of Experiment #7 that relate to atrial pacing are summarized schematically in FIG. 5D (in which a portion of the results of Experiment #5 are also shown, as described above), in which the pacing locations of this experiment are schematically indicated by circled numbers 10 and 11, using the numbers for the angular locations set forth hereinabove in Table 1. FIG. 5D shows a pacing location that achieved atrial pacing. This atrial pacing was achieved using a minimum voltage of 14 V. FIG. 5D also shows an ECG trace for the pacing applied in Experiment #7. The ECG trace was acquired conventionally, using external ECG skin electrodes on the chest.

The pair of pacing electrodes included an anode and a cathode, both of which were disposed sub-annularly, approximately 4-6 mm below the annulus, at Anode Angular Location 10 and Cathode Angular Location 11, respectively. As in Experiments #1, #2, #4, and #5, the electrodes were directly, non-wirelessly connected to the pulse generator.

The pair of pacing electrodes is schematically labeled in FIG. 5D by a connecting line, the ends of which indicate the angular locations of the anode and the cathode. As indicated in the key in FIG. 5D, the endpoints of the lines indicate which electrode was an anode (by a circle) and which electrode was a cathode (by a square). (The lines connect the electrode pairs only schematically, and may or may not indicate the actual conduction paths between the electrode pairs, which were not measured in the experiment.)

A portion of Experiment #7 was designed to assess the feasibility of accurate sensing of a ventricular activation signal and an atrial activation signal in an EGM sensed using two of the electrodes disposed at various electrode locations on the external surface of the frame of the prosthetic aortic valve, without applying pacing. Successful sensing of ventricular activation signals and atrial activation signals was achieved using multiple pairs of electrodes. For example, as schematically labeled in FIG. 5D, both a ventricular intrinsic activation signal (labeled ‘V’ in the EGM) and an atrial intrinsic activation signal (labeled ‘A’ in the EGM) were successfully identified in an EGM sensed using electrodes disposed at Anode Angular Location 10 and Cathode Angular Location 12 (without application of pacing).

Experiment #8

An eighth experiment conducted by the inventors was designed, among other things, to assess the minimal pacing voltage required to achieve ventricular pacing using electrodes disposed at various electrode locations on an external surface of a frame of a prosthetic aortic valve similar to prosthetic aortic valve 20 described hereinabove with reference to FIG. 1. Other than as described below, the eighth experiment was conducted in a similar manner to the horizontal pacing portion of Experiment #2 described hereinabove, and in a similar manner to Experiment #3 described hereinabove. The prosthetic aortic valve had a diameter of 27 mm and included eight electrodes disposed at various respective angular locations with respect to a central longitudinal axis of the frame. The prosthetic aortic valve was implanted transapically in the native aortic valve of two pigs having a weight of 95-100 kg.

Each pair of electrodes included an anode and a cathode, both of which were disposed sub-annularly, approximately 4-6 mm below the annulus, at two different angular locations. As in Experiments #1, #2, and #4, the electrodes were directly, non-wirelessly connected to the pulse generator. The system enabled, by wireless commands from the external transmitter, configuration of each electrode to be a cathode or an anode.

The following Table 14 summarizes the results for each of the pairs of Angular Locations, using the numbers set forth in Table 1 hereinabove:

TABLE 14

| Cathode Angular Location | Anode Angular Location | Min. Voltage For Pacing [V] | Cathode Angular Location | Anode Angular Location | Min. Voltage For Pacing [V] |
|---|---|---|---|---|---|
| 10 | 13 | 14 | 4 | 10 | 1.8 |
| 10 | 12 | 12 | 4 | 3 | 1.8 |
| 10 | 4 | 16 | 4 | 13 | 2 |
| 10 | 5 | 7.5 | 4 | 12 | 2 |
| 10 | 6 | 18 | 4 | 5 | 1.8 |
| 10 | 11 | N* | 4 | 6 | 2 |
| 3 | 13 | 16 | 4 | 11 | 4 |
| 3 | 12 | 10 | 5 | 10 | 2.4 |
| 3 | 4 | 2.4 | 5 | 3 | 2.6 |
| 3 | 5 | 8 | 5 | 13 | 1.9 |
| 3 | 6 | 5.4 | 5 | 12 | 2.6 |
| 3 | 11 | N | 5 | 4 | 1.8 |
| 13 | 10 | 0.8 | 5 | 6 | 2.8 |
| 13 | 3 | 0.8 | 5 | 11 | 3 |
| 13 | 12 | 1 | 6 | 10 | 3.2 |
| 13 | 4 | 1 | 6 | 3 | 3.4 |

TABLE 14-continued

| Cathode Angular Location | Anode Angular Location | Min. Voltage For Pacing [V] | Cathode Angular Location | Anode Angular Location | Min. Voltage For Pacing [V] |
|---|---|---|---|---|---|
| 13 | 5 | 1 | 6 | 13 | 3.4 |
| 13 | 6 | 1 | 6 | 12 | 3.6 |
| 13 | 11 | 1 | 6 | 4 | 2.4 |
| 12 | 10 | 1.6 | 6 | 5 | 3.2 |
| 12 | 3 | 1.8 | 6 | 11 | 3 |
| 12 | 13 | 2 | 11 | 10 | 16 |
| 12 | 4 | 1.8 | 11 | 3 | 16 |
| 12 | 5 | 1.6 | 11 | 13 | 2.6 |
| 12 | 6 | 2.6 | 11 | 12 | 5 |
| 12 | 11 | 1.8 | 11 | 4 | 2.4 |
| | | | 11 | 5 | 9 |
| | | | 11 | 6 | 4.4 |

*N = no pacing

As can be seen, in general (with a few exceptions), Cathode Angular Locations 4, 5, 6, 11, 12, and 13 had lower minimum pacing voltages that Cathode Angular Locations 3 and 10, including for some of the same pairs of Angular Locations at which the polarities were also reversed. As can also be seen, stimulations using a cathode located in the segment stretching between Cathode Angular Locations 5 and 13 yielded the lowest threshold. The inventors observed that the pacing threshold correlates better with the cathode location than with the anode location; in other words, the cathode location is a stronger determinant of the pacing threshold than is the anode location.

In an embodiment, techniques and apparatus described in one or more of the following patents and/or applications, which are assigned to the assignee of the present application and are incorporated herein by reference, are combined with techniques and apparatus described herein:

- U.S. Pat. No. 10,543,083 to Gross
- European Patent Application Publication EP 3508113 A1 to Gross
- U.S. Pat. No. 10,835,750 to Gross
- U.S. Pat. No. 11,013,597 to Gross
- PCT Publication WO 2021/140507 to Gross
- PCT Publication WO 2021/224904 to Gross
- U.S. Pat. No. 11,065,451 to Gross
- U.S. Pat. No. 11,291,844 to Gross
- PCT Publication WO 2022/149130 to Gross
- U.S. Pat. No. 11,975,203 to Gross et al.
- US Patent Application Publication 2025/0058124 to Gross et al.
- PCT Publication WO 2025/041129 to Gross et al.
- U.S. Provisional Application 63/717,923, filed Nov. 8, 2024
- U.S. Provisional Application 63/760,353, filed Feb. 19, 2025
- U.S. application Ser. No. 19/068,620, filed Mar. 3, 2025, now U.S. Pat. No. 12,605,553 to Iamberger et al.
- U.S. Provisional Application 63/809,535, filed May 21, 2025
- U.S. Provisional Application 63/849,212, filed Jul. 23, 2025
- U.S. Provisional Application 63/849,229, filed Jul. 23, 2025

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for delivering ventricular pacing pulses to a heart of a patient, the method comprising:

positioning a first electrode in contact with left ventricular endocardium of a left ventricular outflow tract (LVOT) at a first-electrode site having:

a first-electrode angular location selected from the group of angular locations consisting of: (a) an angular location, with respect to an axis of the LVOT, adjacent to a right side of the muscular part of a ventricular septum, below a right coronary cusp (RCC), and (b) an angular location, with respect to the axis of the LVOT, adjacent to the muscular part of the ventricular septum, below an anterior side of a left coronary cusp (LCC), and a first-electrode vertical location between (a) an upper plane corresponding to an aortic annulus plane and (b) a lower plane parallel to and at a distance below the aortic annulus plane, the distance equal to 8% of a perimeter of an aortic annulus, wherein the aortic annulus plane is the plane defined by respective nadirs of a non-coronary cusp (NCC), the RCC, and the LCC;

positioning a second electrode in contact with the left ventricular endocardium of the LVOT at a second-electrode site having:

a second-electrode angular location with respect to the axis of the LVOT, the second-electrode angular location different from the first-electrode angular location, and a second-electrode vertical location between the upper plane and the lower plane, the second-electrode vertical location the same as or different from the first-electrode vertical location; and activating circuitry to deliver the ventricular pacing pulses by driving a pacing signal between the first and the second electrodes.

2. The method according to claim 1, wherein driving the pacing signal between the first and the second electrodes comprises configuring the first and the second electrodes as a cathode and as an anode, respectively.

3. The method according to claim 1, wherein driving the pacing signal between the first and the second electrodes comprises configuring the first and the second electrodes as an anode and as a cathode, respectively.

4. The method according to claim 1, wherein the second-electrode angular location is along an angular segment extending, with respect to the axis of the LVOT, inclusively, from (a) adjacent to a right fibrous trigone, below the middle of the NCC, (b) around (i) a portion of the NCC, (ii) the LCC, and (iii) a portion of the RCC, to (c) adjacent to the muscular part of the ventricular septum, anterior to a membranous septum (MS), across from a right ventricular outflow tract.

5. The method according to claim 4, wherein the second-electrode angular location is selected from the group of angular locations consisting of: (a) an angular location, with respect to an axis of the LVOT, adjacent to the right side of the muscular part of the ventricular septum, below the RCC, and (b) an angular location, with respect to the axis of the LVOT, adjacent to the muscular part of the ventricular septum, below the anterior side of the LCC.

6. The method according to claim 1, wherein the first-electrode angular location is adjacent to the right side of the muscular part of the ventricular septum, below the RCC.

7. The method according to claim 6, wherein driving the pacing signal between the first and the second electrodes comprises configuring the first and the second electrodes as a cathode and as an anode, respectively.

8. The method according to claim 6, wherein the second-electrode angular location is along an angular segment extending, with respect to the axis of the LVOT, inclusively, from (a) adjacent to a right fibrous trigone, below the middle of the NCC, (b) around (i) a portion of the NCC, (ii) the LCC, and (iii) a portion of the RCC, to (c) adjacent to the muscular part of the ventricular septum, anterior to a membranous septum (MS), across from a right ventricular outflow tract.

9. The method according to claim 6, wherein the first-electrode angular location is adjacent to the muscular part of the ventricular septum, below a left side of the RCC.

10. The method according to claim 9, wherein the second-electrode angular location is adjacent to the muscular part of the ventricular septum, below a right side of the LCC.

11. The method according to claim 6, wherein the first-electrode angular location is adjacent to the muscular part of the ventricular septum, below a mid-portion of the RCC.

12. The method according to claim 11, wherein the second-electrode angular location is selected from the group consisting of: adjacent to the muscular part of the ventricular septum, below a left side of the RCC, and an angular location adjacent to the muscular part of the ventricular septum, below a right side of the LCC.

13. The method according to claim 6, wherein the first-electrode angular location is adjacent to the muscular part of the ventricular septum, anterior to a membranous septum (MS), across from a right ventricular outflow tract.

14. The method according to claim 6, wherein the second-electrode angular location is selected from the group consisting of: adjacent to the muscular part of the ventricular septum, below a left side of the RCC, and an angular location adjacent to the muscular part of the ventricular septum, below a right side of the LCC.

15. The method according to claim 1, wherein the first-electrode angular location is adjacent to the muscular part of the ventricular septum, below the anterior side of the LCC.

16. The method according to claim 15, wherein driving the pacing signal between the first and the second electrodes comprises configuring the first and the second electrodes as a cathode and as an anode, respectively.

17. The method according to claim 15, wherein the second-electrode angular location is along an angular segment extending, with respect to the axis of the LVOT, inclusively, from (a) adjacent to a right fibrous trigone, below the middle of the NCC, (b) around (i) a portion of the NCC, (ii) the LCC, and (iii) a portion of the RCC, to (c) adjacent to the muscular part of the ventricular septum, anterior to a membranous septum (MS), across from a right ventricular outflow tract.

18. The method according to claim 15, wherein the first-electrode angular location is adjacent to the left lateral end of the muscular part of the ventricular septum closest to a left fibrous trigone.

19. The method according to claim 15, wherein the first-electrode angular location is adjacent to the muscular part of the ventricular septum, below a right side of the LCC.

20. The method according to claim 1, wherein the second-electrode vertical location is the same as the first-electrode vertical location.

21. The method according to claim 1, wherein positioning the first electrode at the first-electrode site and positioning the second electrode at the second-electrode site comprise:

delivering a frame to an aortic position in the heart in a constrained delivery configuration, the frame including interconnected stent struts, wherein the first and the second electrodes are coupled to the frame; and transitioning the frame to an expanded deployment configuration, in which the frame positions and holds the first and the second electrodes in contact with the left ventricular endocardium of the LVOT at the first-electrode and the second-electrode sites, respectively.

22. The method according to claim 21, wherein delivering the frame comprises delivering a prosthetic aortic valve to the native aortic valve, the prosthetic aortic valve including the frame and a plurality of prosthetic leaflets coupled to the frame so as to allow blood flow in a downstream direction and inhibit blood flow in an upstream direction.

23. The method according to claim 1, wherein positioning the first electrode at the first-electrode site and positioning the second electrode at the second-electrode site comprise:

delivering a support to an aortic position in the heart in a constrained delivery configuration, wherein the first and the second electrodes are coupled to the support; and transitioning the support to an expanded deployment configuration, in which the support positions and holds the first and the second electrodes in contact with the left ventricular endocardium of the LVOT at the first-electrode and the second-electrode sites, respectively.

24. The method according to claim 23, further comprising introducing a prosthetic aortic valve into a body of the patient and placing the prosthetic aortic valve within the support, the prosthetic aortic valve including a plurality of prosthetic leaflets arranged so as to allow blood flow in a downstream direction and inhibit blood flow in an upstream direction.

25. The method according to claim 1, wherein activating the circuitry comprises activating the circuitry to deliver the ventricular pacing pulses comprises applying each of the pulses with a voltage of no more than 25 V.

26. The method according to claim 25, wherein the voltage is no more than 12 V.

27. The method according to claim 25, wherein activating the circuitry comprises activating the circuitry to deliver the ventricular pacing pulses comprises applying each of the pulses with a pulse duration of no more than 0.7 milliseconds.

28. The method according to claim 1, wherein activating the circuitry comprises activating the circuitry to deliver the ventricular pacing pulses comprises applying each of the pulses with an amplitude of no more than 50 milliamps.

29. The method according to claim 28, wherein activating the circuitry comprises activating the circuitry to deliver the ventricular pacing pulses comprises applying each of the pulses with a pulse duration of no more than 0.7 milliseconds.

* * * * *